United States Patent
Shinde et al.

(10) Patent No.: US 11,197,474 B2
(45) Date of Patent: *Dec. 14, 2021

(54) DRIED CHLORELLA BASED COMPOSITIONS AND METHODS FOR PLANTS

(71) Applicant: HELIAE DEVELOPMENT LLC, Gilbert, AZ (US)

(72) Inventors: Sandip Shinde, Gilbert, AZ (US); Laura Carney, Chandler, AZ (US); Stephen Ventre, Mesa, AZ (US)

(73) Assignee: Heliae Development, LLC, Gilbert, AZ (US)

( * ) Notice: Subject to any disclaimer, the term of this patent is extended or adjusted under 35 U.S.C. 154(b) by 179 days.

This patent is subject to a terminal disclaimer.

(21) Appl. No.: 16/064,094

(22) PCT Filed: Jan. 25, 2017

(86) PCT No.: PCT/US2017/014843
§ 371 (c)(1),
(2) Date: Jun. 20, 2018

(87) PCT Pub. No.: WO2017/132204
PCT Pub. Date: Aug. 3, 2017

(65) Prior Publication Data
US 2019/0000091 A1    Jan. 3, 2019

Related U.S. Application Data

(60) Provisional application No. 62/288,519, filed on Jan. 29, 2016.

(51) Int. Cl.
| | | |
|---|---|---|
| *A01N 65/03* | (2009.01) | |
| *A01N 25/00* | (2006.01) | |
| *A01H 5/10* | (2018.01) | |
| *C12N 1/12* | (2006.01) | |

(52) U.S. Cl.
CPC .............. *A01N 25/00* (2013.01); *A01H 5/10* (2013.01); *C12N 1/12* (2013.01); *A01N 65/03* (2013.01)

(58) Field of Classification Search
None
See application file for complete search history.

(56) References Cited

U.S. PATENT DOCUMENTS

| | | | | |
|---|---|---|---|---|
| 4,551,164 A | * | 11/1985 | Tenzer | C05F 11/08 71/6 |
| 5,130,242 A | * | 7/1992 | Barclay | A61K 31/20 435/134 |
| 2004/0049062 A1 | * | 3/2004 | Bijl | A23K 20/158 554/1 |
| 2012/0094831 A1 | * | 4/2012 | Bartley, Jr. | A01N 65/00 504/101 |
| 2016/0165895 A1 | | 6/2016 | Shinde et al. | |
| 2016/0165896 A1 | | 6/2016 | Shinde et al. | |
| 2016/0165897 A1 | | 6/2016 | Shinde et al. | |

FOREIGN PATENT DOCUMENTS

| | | | |
|---|---|---|---|
| KR | 20100134214 | | 12/2010 |
| WO | 2014074769 | | 5/2014 |
| WO | WO 2014/074769 | * | 5/2014 |
| WO | 2016100550 | | 6/2016 |

OTHER PUBLICATIONS

Higgins et al., PLoS ONE 9(5): e96807 (2014).*
Lin et al., Food Microstructure 4: 341-348 (1985).*
Fayza, et al. "Effect of Chlorella vulgaris as Bio-Fertilizer on Growth Parameters and Metabolic Aspects of Lettuce Plant." Journal of Agriculture and Social Sciences. vol. 4, Jan. 1, 2008 (Jan. 1, 2008), pp. 165-16955360081.
Yandu Lu, et al. "Phytohormones in Microalgae: a new opportunity for microalgal biotechnology?" Trends in Plant Science. vol. 20, No. 5, May 1, 2015 (May 1, 2015), pp. 273-282.
L.P. Lin. "Microstructure of Spray-Dried and Freeze-Dried Microalgal Powders", Food Structure, vol. 4, No. 2, Jan. 1, 1985 (Jan. 1, 1985), pp. 341-348.
Kitano M et al. "Degradation of Chlorella Cell During Composting", Journal of Biotechnology, Elsevier, Amsterdam NL, vol. 66, No. 2-3, Dec. 11, 1998 (Dec. 11, 1998), pp. 187-193.
PCT International Search Report and Written Opinion dated Apr. 10, 2017.

* cited by examiner

*Primary Examiner* — Erin M. Bowers
(74) *Attorney, Agent, or Firm* — Helia Development, LLC; Adam L. Lunceford; Veronica-Adele R. Cao

(57) ABSTRACT

Compositions suitable for application to plants and seeds comprising dried *Chlorella* cells are disclosed. Methods of preparing and applying compositions of dried *Chlorella* cells to plants and seeds to enhance at least one characteristic of a plant are disclosed.

20 Claims, No Drawings

DRIED CHLORELLA BASED COMPOSITIONS AND METHODS FOR PLANTS

CROSS REFERENCE TO RELATED APPLICATIONS

The present application is a U.S. National Stage entry under 35 U.S.C. § 371 of International Application No. PCT/US2017/014843, filed on Jan. 25, 2017, designating the United States of America and published in English on Aug. 3, 2017 as WO2017/132204 which in turns claims priority to U.S. Provisional Application No. 62/288,519, filed Jan. 29, 2016, entitled Dried Microalgae Based Composition, And Methods of its Preparation and Application to Plants. The entire contents of all of the foregoing are hereby incorporated by reference herein.

BACKGROUND

Seed emergence occurs as an immature plant breaks out of its seed coat, typically followed by the rising of a stem out of the soil. The first leaves that appear on many seedlings are the so-called seed leaves, or cotyledons, which often bear little resemblance to the later leaves. Shortly after the first true leaves, which are more or less typical of the plant, appear the cotyledons will drop off. Germination of seeds is a complex physiological process triggered by imbibition of water after possible dormancy mechanisms have been released by appropriate triggers. Under favorable conditions rapid expansion growth of the embryo culminates in rupture of the covering layers and emergence of the radicle. A number of agents have been proposed as modulators of seed emergence. Temperature and moisture modulation are common methods of affecting seed emergence. Addition of nutrients to the soil has also been proposed to promote emergence of seeds of certain plants.

Similarly, the growth and fruit production of a mature plant is also a complex physiological process involving inputs and pathways in the roots, shoot, and leaves. Whether at a commercial or home garden scale, growers are constantly striving to optimize the yield and quality of a crop to ensure a high return on the investment made in every growth season. As the population increases and the demand for raw plant materials goes up for the food and renewable technologies markets, the importance of efficient agricultural production intensifies. The influence of the environment on a plant's health and production has resulted in a need for strategies during the growth season which allow the plants to compensate for the influence of the environment and maximize production. Addition of nutrients to the soil or application to the foliage has also been proposed to promote yield and quality in certain plants. The effectiveness can be attributable to the ingredients or the method of preparing the product. Increasing the effectiveness of a product can reduce the amount of the product needed and increase efficiency of the agricultural process.

SUMMARY

Embodiments are described for applying a composition comprising dried microalgae to a plant or seed to enhance at least one characteristic of the plant. The compositions can include cells from the genus *Chlorella* that have been subjected to a drying process. The composition can include *Chlorella* as the primary or sole active ingredient, or in combination with other active ingredients such as, but not limited to, extracts from macroalgae, extracts from microalgae, and non-*Chlorella* microalgae. The compositions may be applied to seeds and plants in a plurality of manners such as, but not limited to, seed coating, seed soaking, hydroponic administration, administration to a solid growth medium, and mixing a solid growth medium. In some embodiments, the composition may comprise mixotrophically cultured *Chlorella*. Depending on the desired characteristics of the composition, a variety of methods for drying the microalgae are described. Additionally, the composition may further comprise stabilizers and other plant nutrients.

For example, some embodiments of the invention relate to a method for enhancing emerge of a plant from seed. In one non-limiting embodiment, a method of plant enhancement may comprise administering to a plant, seedling, or seed a composition comprising 0.1-20% by volume of dried *Chlorella* cells to enhance at least one plant characteristic. In some embodiments, the concentration of dried *Chlorella* cells may be 1-5% by volume.

In some embodiments, the *Chlorella* may be dried by at least one method selected from the group consisting of: freeze drying, spray drying, drum drying, crossflow air drying, solar drying, thin film convection oven drying, vacuum shelf drying, pulse combustion drying, flash drying, furnace drying, belt conveyor drying, and refractance window drying. In some embodiments, the *Chlorella* cells may be cultured in mixotrophic conditions. In some embodiments, the mixotrophic condition may comprise culturing *Chlorella* cells in a suitable culture medium for a culture length of 7-14 days, at a temperature between 20 and 30° C., at a pH between 6.5 and 8.5, and a dissolved oxygen concentration between 0.1 and 4 mg/L. In some embodiments, the *Chlorella* cells may be cultured in non-axenic mixotrophic conditions. In some embodiments, the *Chlorella* cells may be cultured with acetic acid or acetate as the organic carbon source.

In some embodiments, the administering step may be selected from the group consisting of; coating a seed with the composition prior to planting; soaking a seed in a solution of water and the composition prior to planting; contacting a solid growth medium in an immediate vicinity of a planted seed with an effective amount of the composition; contacting roots of a plant with an effective amount of the composition hydroponically; administering an effective amount to a solid growth medium prior to or after the planting of a seed, seedling, or plant; and mixing an effective amount of the composition in a suitable solid growth medium prior to planting a seed, seedling, or plan.

In some embodiments, the solid growth medium may comprise at least one from the group consisting of: soil, potting mix, compost, or inert hydroponic material. In some embodiments, the composition may be administered to the solid growth medium by mixing the composition with water and distributing through a system selected from a low volume irrigation system, a soil drench application, and an aerial spraying system.

In some embodiments, the plant may be a member of a plant family selected from: Solanaceae, Fabaceae (Leguminosae), Poaceae, Roasaceae, Vitaceae, Brassicaeae (Cruciferae), Caricaceae, Malvaceae, Sapindaceae, Anacardiaceae, Rutaceae, Moraceae, Convolvulaceae, Lamiaceae, Verbenaceae, Pedaliaceae, Asteraceae (Compositae), Apiaceae (Umbelliferae), Araliaceae, Oleaceae, Ericaceae, Actinidaceae, Cactaceae, Chenopodiaceae, Polygonaceae, Theaceae, Lecythidaceae, Rubiaceae, Paveraceae, Illiciaceae, Grossulariaceae, Myrtaceae, Juglandaceae, Bertulaceae, Cucurbitaceae, Asparagaceae (Liliaceae), Alliaceae (Liliceae), Bromeliaceae, Zingieraceae, Muscaceae, Areaceae, Dioscoreaceae, Myristicaceae, Annonaceae, Euphorbiaceae, Lauraceae, Peperaceae, and Proteaceae.

In some embodiments, the composition may further comprise water and at least one stabilizer suitable for plants selected from the group consisting of: potassium sorbate, phosphoric acid, ascorbic acid, sodium benzoate, and citric acid. In some embodiments, the composition may not contain an active ingredient for enhancing the plant characteristic other than the dried *Chlorella* cells. In some embodiments, the composition may further comprise at least one selected from the group consisting of: nitrogen, phosphorus, potassium, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium.

In some embodiments, the enhancement of the at least one plant characteristic may be determined by comparison of a treated plant with a substantially identical untreated plant, and wherein a quantifiable different of at least 10% is observed for the at least one plant characteristic. In some embodiments, the plant characteristic may be selected from the group consisting of: seed germination rate, seed germination time, seedling emergence, seedling emergence time, seedling size, seedling vigor, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. In some embodiments, the dried *Chlorella* cells may comprise 1-8% moisture on a wet basis.

In another non-limiting embodiment, a composition may comprise: 0.1-20% by volume of dried mixotrophically cultured *Chlorella* cells suitable for application to plants, wherein the mixotrophically cultured *Chlorella* cells comprise 1-8% moisture on a wet basis. In some embodiments, the composition may further comprise at least one selected from the group consisting of: nitrogen, phosphorus, potassium, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium.

In some embodiments, the composition may further comprise water. In some embodiments, the composition may further comprise soil, potting mix, compost, inert hydroponic material, or combinations thereof. In some embodiments, the composition may further comprise at least one of a binder, filler, solvent, thickener, colouring agent, antifoaming agent, biocide, surfactant, and pigment suitable for a seed coating.

In some embodiments, the *Chlorella* cells may be intact. In some embodiments, the *Chlorella* cells may be lysed or disrupted. In some embodiments, the *Chlorella* cells may be cultured in non-axenic mixotrophic conditions. In some embodiments, the *Chlorella* cells are cultured with acetic acid or acetate as an organic carbon source.

In another non-limiting embodiment, a method of preparing a composition may comprise: drying mixotrophically cultured *Chlorella* cells to a moisture content of 1-8% on a wet basis; and storing the dried cells in a container. In some embodiments, the method may further comprise mixing the dried *Chlorella* cells at a concentration of 0.1-20% by volume with at least one of a solid growth medium selected from the group consisting of: soil, potting mix, compost, and inert hydroponic material.

In some embodiments, the method may further comprise mixing the composition with at least one stabilizer suitable for plants selected from group consisting of: potassium sorbate, phosphoric acid, ascorbic acid, sodium benzoate, and citric acid. In some embodiments, the method may further comprise mixing the composition with at least one other component suitable for coating seeds. In some embodiments, the method may further comprise mixing the composition with at least one selected from the group consisting of: nitrogen, phosphorus, potassium, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium.

In another non-limiting embodiment, a method of making a composition for enhancing a characteristic of a plant may comprise: subjecting *Chlorella* cells to a drying means to produce dried *Chlorella* cells with a moisture content of 1-15%; and forming a composition comprising 0.1-20% by volume of dried *Chlorella* cells, wherein the composition is suitable to administer to a plant, seedling, or seed to enhance at least one plant characteristic. In some embodiments, the drying means may lyse or disrupt the *Chlorella* cells. In some embodiments, the drying means may increase the pore size of the *Chlorella* cells. In some embodiments, the drying means may reduce at least one of protein and pigment concentrations of the *Chlorella* cells.

DETAILED DESCRIPTION

Many plants can benefit from the application of compositions that provide a bio-stimulatory effect. Non-limiting examples of plant families that can benefit from such compositions can comprise: Solanaceae, Fabaceae (Leguminosae), Poaceae, Rosaceae, Vitaceae, Brassicaeae (Cruciferae), Caricaceae, Malvaceae, Sapindaceae, Anacardiaceae, Rutaceae, Moraceae, Convolvulaceae, Lamiaceae, Verbenaceae, Pedaliaceae, Asteraceae (Compositae), Apiaceae (Umbelliferae), Araliaceae, Oleaceae, Ericaceae, Actinidaceae, Cactaceae, Chenopodiaceae, Polygonaceae, Theaceae, Lecythidaceae, Rubiaceae, Papveraceae, Illiciaceae Grossulariaceae, Myrtaceae, Juglandaceae, Bertulaceae, Cucurbitaceae, Asparagaceae (Liliaceae), Alliaceae (Liliceae), Bromeliaceae, Zingieraceae, Muscaceae, Areaceae, Dioscoreaceae, Myristicaceae, Annonaceae, Euphorbiaceae, Lauraceae, Piperaceae, and Proteaceae.

The Fabaceae plant family (also known as the Leguminosae) comprises the third largest plant family with over 18,000 species, including a number of important agricultural and food plants. Taxonomically classified in the Plantae kingdom, Tracheobionta (subkingdom), Spermatophyta (superdivision), Magnoliophyta (division), Manoliopsida (class), Rosidae (subclass), and Fabales (order), the Fabaceae family includes, but is not limited to, soybeans, beans, green beans, peas, chickpeas, alfalfa, peanuts, sweet peas, carob, and liquorice. Plants in the Fabaceae family can range in size and type, including but not limited to, trees, small annual herbs, shrubs, and vines, and typically develop legumes. Plants in the Fabaceae family can be found on all the continents, excluding Antarctica, and thus have a widespread importance in agriculture across the globe. Besides food, plants in the Fabaceae family can be used to produce natural gums, dyes, and ornamentals.

The Solanaceae plant family includes a large number of agricultural crops, medicinal plants, spices, and ornamentals in its over 2,500 species. Taxonomically classified in the Plantae kingdom, Tracheobionta (subkingdom), Spermatophyta (superdivision), Magnoliophyta (division), Manoliopsida (class), Asteridae (subclass), and Solanales (order), the Solanaceae family includes, but is not limited to, potatoes, tomatoes, eggplants, various peppers, tobacco, and petunias. Plants in the Solanaceae can be found on all the continents, excluding Antarctica, and thus have a widespread importance in agriculture across the globe.

The Poaceae plant family supplies food, building materials, and feedstock for fuel processing. Taxonomically classified in the Plantae kingdom, Tracheobionta (subkingdom), Spermatophyta (superdivision), Magnoliophyta (division), Liliopsida (class), Commelinidae (subclass), and Cyperales (order), the Poaceae family includes, but is not limited to, flowering plants, grasses, and cereal crops such as barely, corn, lemongrass, millet, oat, rye, rice, wheat, sugarcane, and sorghum. Types of turf grass found in Arizona include, but are not limited to, hybrid Bermuda grasses (e.g., 328 tifgrn, 419 tifway, tif sport).

The Rosaceae plant family includes flowering plants, herbs, shrubs, and trees. Taxonomically classified in the Plantae kingdom, Tracheobionta (subkingdom), Spermatophyta (superdivision), Magnoliophyta (division), Magnoliopsida (class), Rosidae (subclass), and Rosales (order), the Rosaceae family includes, but is not limited to, almond, apple, apricot, blackberry, cherry, nectarine, peach, plum, raspberry, strawberry, and quince.

The Vitaceae plant family includes flowering plants and vines. Taxonomically classified in the Plantae kingdom, Tracheobionta (subkingdom), Spermatophyta (superdivision), Magnoliophyta (division), Magnoliopsida (class), Rosidae (subclass), and Rhammales (order), the Vitaceae family includes, but is not limited to, grapes.

Particularly important to plant production is the beginning stage of growth where the plant emerges and matures into establishment. A method of treating a seed, seedling, or plant to directly improve the germination, emergence, and maturation of the plant; or to indirectly enhance the microbial soil community surrounding the seed or seedling is therefore valuable in starting the plant on the path to marketable production. The standard typically used for assessing emergence is the achievement of the hypocotyl stage, where a stem is visibly protruding from the soil. The standard typically used for assessing maturation is the achievement of the cotyledon stage, where two leaves visibly form on the emerged stem.

Also important in the production of fruit from plants is the yield and quality of fruit, which can be expressed in terms of, for example, the number, weight, color, firmness, ripeness, moisture, degree of insect infestation, degree of disease or rot, and/or degree of sunburn of the fruit. A method of treating a plant to directly improve the characteristics of the plant, or to indirectly enhance the biochemistry of the plant for photosynthetic capabilities and health of the plant's leaves, roots, and shoot to enable robust production of fruit is therefore valuable in increasing the efficiency of marketable production. Marketable and unmarketable designations can apply to both the plant and fruit, and can be defined differently based on the end use of the product, such as but not limited to, fresh market produce and processing for inclusion as an ingredient in a composition. The marketable determination can assess such qualities as, but not limited to, color, insect damage, blossom end rot, softness, and sunburn. The term total production can incorporate both marketable and unmarketable plants and fruit. The ratio of marketable plants or fruit to unmarketable plants or fruit can be referred to as utilization and expressed as a percentage. The utilization can be used as an indicator of the efficiency of the agricultural process as it shows the successful production of marketable plants or fruit, which will obtain the highest financial return for the grower, whereas total production will not necessarily provide such an indication.

To achieve such improvements in health, emergence, maturation, yield, and quality of plants, embodiments of the invention provide microalgae based compositions, methods of preparing microalgae based compositions, and methods of applying the microalgae based compositions to plants. In one non-limiting embodiments, the microalgae of the composition can comprise *Chlorella* sp. cultured in mixotrophic conditions, which comprises a culture medium primarily comprised of water with trace nutrients (e.g., nitrates, phosphates, vitamins, metals found in BG-11 recipe (available from UTEX The Culture Collection of Algae at the University of Texas at Austin, Austin, Tex.)), light as an energy source for photosynthesis, organic carbon (e.g., acetate, acetic acid) as both an energy source and a source of carbon. In some embodiments, the *Chlorella* can be cultured in non-axenic mixotrophic conditions in the presence of contaminating organisms such as, but not limited to, bacteria. Methods of culturing such microalgae in non-axenic mixotrophic conditions and a list of other microalgae capable of mixotrophic growth can be found in WO2014/074769A2 (Ganuza, et al.), hereby incorporated by reference.

In one non-limiting example of mixotrophic culturing of *Chlorella* for the described method of preparation of a composition for application to plants, the *Chlorella* is cultured in a BG-11 culture media or media derived from BG-11 culture media (e.g., in which additional component(s) are added to the media and/or one or more elements of the media is increased by 5%, 10%, 15%, 20%, 25%, 33%, 50%, or more over unmodified BG-11 media) for a culture length of 7-14 days in an open culturing vessel. The temperature can range from 20-30° C. and the pH from 6.5-8.5. The dissolved oxygen concentration can range from 0.1-4 mg/L. The culture receives acetic acid or acetate as a source of organic carbon supplying both carbon and an energy source to the *Chlorella* cells, and is supplied to the culture in a feed with a concentration in the range of 10-90% by a pH auxostat system. The culture receives natural sunlight (comprising photosynthetically active radiation) as source of energy. Mixing is provided by air sparging through aerotube, and fluid propulsion by thrusters submerged in the liquid culture; or in the alternative embodiment both mixing and infusion of gases is provided by an aerator (e.g., Aire-O2® Series 275 Aspirator Aerator available from Aeration Industries International, Chaska, Minn. USA).

By artificially controlling aspects of the microalgae culturing process such as the organic carbon feed, oxygen levels, pH, and light, the culturing process differs from the culturing process that the microalgae (e.g., *Chlorella*) experiences in nature. In addition to controlling various aspects of the culturing process, intervention by human operators or automated systems occurs during the non-axenic mixotrophic culturing of microalgae through contamination control methods to prevent the microalgae from being overrun and outcompeted by contaminating organisms (e.g., fungi, bacteria). Contamination control methods for microalgae cultures are known in the art and such suitable contamination control methods for non-axenic mixotrophic microalgae cultures are disclosed in WO2014/074769A2 (Ganuza, et al.) and U.S. Pat. No. 9,181,523 B1 (Ganuza, et al.), hereby incorporated by reference. By intervening in the microalgae culturing process, the impact of the contaminating microorganisms can be mitigated by suppressing the proliferation of containing organism populations and the effect on the microalgal cells (e.g., lysing, infection, death, clumping). Thus, through artificial control of aspects of the culturing process and intervening in the culturing process with contamination control methods, the microalgae culture produced as a whole and used in the described inventive compositions differs from the culture that results from a microalgae culturing process that occurs in nature.

In the alternative, the method of culturing *Chlorella* or other microalgae mixotrophically can comprise other known sources of organic carbon or combinations of organic carbon sources, such as: ammonium linoleate, arabinose, arginine, aspartic acid, butyric acid, cellulose, citric acid, ethanol, fructose, fatty acids, galactose, glucose, glycerol, glycine, lactic acid, lactose, maleic acid, maltose, mannose, methanol, molasses, peptone, plant based hydrolyzate, proline, propionic acid, ribose, sacchrose, partial or complete hydrolysates of starch, sucrose, tartaric, TCA-cycle organic acids, thin stillage, urea, industrial waste solutions, and yeast extract; as well as other known methods of mixing, methods of organic carbon supply, lighting, culture media, nutrient stocks, culturing vessels, and optimization of the culture parameters such as but not limited to temperature, pH, dissolved oxygen, and dissolved carbon dioxide. The mixotrophic microalgae culture can be harvested from the culturing vessel and/or concentrated by means known in the art, such as but not limited to, settling, centrifugation, filtration, and electrodewatering before drying.

During the mixotrophic culturing process the *Chlorella* culture can also comprise cell debris and compounds excreted from the *Chlorella* cells into the culture medium. The output of the *Chlorella* mixotrophic culturing process provides the active ingredient for a composition that is applied to plants for improving at least one plant performance characteristic such as, for example, emergence, maturation, yield, quality, and the like. Typically, the composition is applied without separate addition to or supplementation of the composition with other active ingredients not found in the mixotrophic *Chlorella* whole cells and accompanying culture medium from the mixotrophic culturing process such as, but not limited to: non-*Chlorella* microalgae cells, microalgae extracts, macroalgae, macroalgae extracts, liquid fertilizers, granular fertilizers, mineral complexes (e.g., calcium, sodium, zinc, manganese, cobalt, silicon), fungi, bacteria, nematodes, protozoa, digestate solids, chemicals (e.g., ethanolamine, borax, boric acid), humic acid, nitrogen and nitrogen derivatives, phosphorus rock, pesticides, herbicides, insecticides, enzymes, plant fiber (e.g., coconut fiber); however, in some embodiments the augmentation of the base composition with any of the foregoing is contemplated.

The term "microalgae" refers to microscopic single cell organisms such as microalgae, cyanobacteria, algae, diatoms, dinoflagellates, freshwater organisms, marine organisms, or other similar single cell organisms capable of growth in phototrophic, mixotrophic, or heterotrophic culture conditions. Taxonomic classification has also been in flux for organisms in the genus *Schizochytrium*. Some organisms previously classified as *Schizochytrium* have been reclassified as *Aurantiochytrium*, *Thraustochytrium*, or *Oblongichytrium*. See Yokoyama et al. Taxonomic rearrangement of the genus *Schizochytrium* sensu lato based on morphology, chemotaxonomic characteristics, and 18S rRNA gene phylogeny (Thrausochytriaceae, Labyrinthulomycetes): emendation for *Schizochytrium* and erection of *Aurantiochytrium* and *Oblongichytrium* gen. nov. *Mycoscience* (2007) 48:199-211. Those of skill in the art will recognize that *Schizochytrium*, *Aurantiochytrium*, *Thraustochytrium*, and *Oblongichytrium* appear closely related in many taxonomic classification trees for microalgae, and strains and species may be re-classified from time to time. Thus, for references throughout the instant specification for *Schizochytrium*, it is recognized that microalgae strains in related taxonomic classifications with similar characteristics to *Schizochytrium* would reasonably be expected to produce similar results.

In some embodiments, microalgae biomass, excreted product, or extracts may also be sourced from multiple types of microalgae, to make a composition that is beneficial when applied to plants or soil. Non-limiting examples of microalgae that can be used in the compositions and methods of the present invention comprise microalgae in the classes: Eustigmatophyceae, Chlorophyceae, Prasinophyceae, Haptophyceae, Cyanidiophyceae, Prymnesiophyceae, Porphyridiophyceae, Labyrinthulomycetes, Trebouxiophyceae, Bacillariophyceae, and Cyanophyceae. The class Cyanidiophyceae includes species of *Galdieria*. The class Chlorophyceae includes species of *Haematococcus, Scenedesmus, Chlamydomonas*, and *Micractinium*. The class Prymnesiophyceae includes species of *Isochrysis* and *Pavlova*. The class Eustigmatophyceae includes species of *Nannochloropsis*. The class Porphyridiophyceae includes species of *Porphyridium*. The class Labyrinthulomycetes includes species of *Schizochytrium* and *Aurantiochytrium*. The class Prasinophyceae includes species of *Tetraselmis*. The class Trebouxiophyceae includes species of *Chlorella*. The class Bacillariophyceae includes species of *Phaeodactylum*. The class Cyanophyceae includes species of *Spirulina*.

Non-limiting examples of microalgae species that can be used in the compositions and methods of the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Aurantiochytrium* sp., *Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomonas* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella spha-* erica, *Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Galdieria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrine, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phagus, Phormidium, Platymonas* sp., *Pleurochrysis camerae, Pleurochrysis dentate, Pleurochrysis* sp., *Porphyridium* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii,* and *Viridiella fridericiana.*

In some embodiments, the composition may comprise two or more different microalgae species. In some embodiments, the microalgae population may be divided evenly between two or more different microalgae species. In some embodiments, the microalgae population may be divided unevenly between two or more different microalgae species.

In some embodiments, microalgae cells may be mixed with extracts from other plants, microalgae, macroalgae, seaweeds, and kelp. Non-limiting examples of seaweeds/macroalgae that may be processed through extraction and combined with microalgae cells may comprise species of *Kappaphycus, Ascophyllum, Macrocystis, Fucus, Laminaria, Sargassum, Turbinaria,* and *Durvilea*. In some embodiments, the microalgae composition can be supplemented with a supplemental nutrient such as nitrogen, phosphorus, or potassium to increase the levels within the composition to at least 1% of the total composition (i.e., addition of N, P, or K to increase levels at least 1-0-0, 0-1-0, 0-0-1, or combinations thereof). In some embodiments, the microalgae composition may be supplemented with nutrients such as, but not limited to, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium. In some embodiments, the supplemented nutrient is not uptaken, chelated, or absorbed by the microalgae. In some embodiments, the concentration of the supplemental nutrient may comprise 1-50 g per 100 g of the composition.

In some embodiments, mixotrophic *Chlorella* is the dominant microalgae species in the composition. In some embodiments, the microalgae population of the composition is substantially mixotrophic *Chlorella*. In some embodiments, mixotrophic or non-mixotrophic *Chlorella* comprises at least 90% of the microalgae population of the composition. In some embodiments, mixotrophic or non-mixotrophic *Chlorella* comprises at least 91% of the microalgae population of the composition. In some embodiments, mixotrophic or non-mixotrophic *Chlorella* comprises at least 92% of the microalgae population of the composition. In some embodiments, mixotrophic or non-mixotrophic *Chlorella* comprises at least 93% of the microalgae population of the composition. In some embodiments, mixotrophic or non-mixotrophic *Chlorella* comprises at least 94% of the microalgae population of the composition. In some embodiments, mixotrophic or non-mixotrophic *Chlorella* comprises at least 95% of the microalgae population of the composition. In some embodiments, mixotrophic or non-mixotrophic *Chlorella* comprises at least 96% of the microalgae population of the composition. In some embodiments, mixotrophic or non-mixotrophic *Chlorella* comprises at least 97% of the microalgae population of the composition. In some embodiments, mixotrophic or non-mixotrophic *Chlorella* comprises at least 98% of the microalgae population of the composition. In some embodiments, mixotrophic or non-mixotrophic *Chlorella* comprises at least 99% of the microalgae population of the composition. Compositions having at least 99% of a *Chlorella* microalgae strain (e.g., at least 99.3%, at least 99.5%, or even at least 99.9%), such as mixotrophic *Chlorella*, can be considered to have a single algal species in the composition. In one aspect, the composition lacks any detectable amount of any other microalgae species. In another aspect, the composition lacks any amount of any other microorganism (e.g., bacteria) in the composition other than the desired *Chlorella* microalgae that is above 1% of the composition by weight.

The mixotrophic *Chlorella* resulting from the culturing stage consists of whole cells with the proximate analysis shown in Table 1, fatty acid profile shown in Table 2, and results of further analysis shown in Examples 1-3.

TABLE 1

| | Range |
|---|---|
| Moisture & Volatiles | 1-2% |
| Ash Content | 3-4.5% |
| Carbohydrates (calculated) | 30-36% |
| % Protein (Leco) | 15-45% |
| % Lipids (AOAC) | 5-20% |

TABLE 2

| Analyte | Range (%) |
| --- | --- |
| C16 Palmitic Acid | 0.1-4 |
| C18:1n9c Oleic acid (Omega-9) | 0.1-2 |
| C18:2n6c Linoleic acid (Omega-6) | 0.1-5 |
| C18:3n3 Alpha-Linoleic acid (Omega-3) | 0.1-2 |
| Other | 0.1-4 |
| Total | 0.5-17 |

The mixotrophic *Chlorella* cells can also contain detectable levels of phytohormones, such as but not limited to: abscisic acid and metabolites, which are known to be related to the stomatal apparatus function, growth inhibition, and seed dormancy; cytokinins, which are known to be related to cell division, bud development, development of the leaf blade, and senescence retardation; auxins, which are known to be related to elongation growth, differentiation of phloem elements, apical dominance, tropism, and initial root formation; and gibberellins, which are known to be related to stem elongation and initiation of seed germination.

In some embodiments, the mixotrophic *Chlorella* can comprise abscisic acid and abscisic acid metabolites in a range of 0.1-45 ng/g dry weight (DW). In some embodiments, the mixotrophic *Chlorella* can comprise cytokinins in a range of 60-300 ng/g dry weight (DW). In some embodiments, the mixotrophic *Chlorella* can comprise cytokinins in a range of 0.1-100 ng/g dry weight (DW). In some embodiments, the mixotrophic *Chlorella* can comprise auxins in a range of 400-815 ng/g dry weight (DW). In some embodiments, the mixotrophic *Chlorella* can comprise auxins in a range of 800-1400 ng/g dry weight (DW). In some embodiments, the mixotrophic *Chlorella* can comprise gibberellins in a range of 0.1-15 ng/g dry weight (DW). In some embodiments, the mixotrophic *Chlorella* can comprise specific phytohormones in the ranges shown in Table 3.

In some embodiments, the mixotrophic *Chlorella* can comprise abscisic acid and abscisic acid metabolites in a range of 0.1-1 ng/g fresh weight (FW). In some embodiments, the mixotrophic *Chlorella* can comprise cytokinins in a range of 10-30 ng/g fresh weight (FW). In some embodiments, the mixotrophic *Chlorella* can comprise cytokinins in a range of 0.1-10 ng/g fresh weight (FW). In some embodiments, the mixotrophic *Chlorella* can comprise auxins in a range of 1-30 ng/g fresh weight (FW). In some embodiments, the mixotrophic *Chlorella* can comprise auxins in a range of 30-150 ng/g fresh weight (FW). In some embodiments, the mixotrophic *Chlorella* can comprise gibberellins in a range of 0.1-1 ng/g fresh weight (FW).

TABLE 3

| Metabolite | Range (ng/g DW) |
| --- | --- |
| cis-Abscisic acid | 0.1-13 |
| Abscisic acid glucose ester | 0.1-5 |
| Phaseic acid | 0.1-9 |
| Neo-Phaseic acid | 0.1-5 |
| trans-Abscisic acid | 0.1-8 |
| (trans) Zeatin | 0.1-5 |
| (cis) Zeatin | 0.1-16 |
| (trans) Zeatin riboside | 4-20 |
| (cis) Zeatin riboside | 30-250 |
| Dihydrozeatin riboside | 0.1-2 |
| Isopentenyladenine | 0.1-8 |
| Isopentenyladenosine | 1-15 |
| Indole-3-acetic acid | 400-815 |
| N-(Indole-3-yl-acetyl)-alanine | 0.1-5 |
| gibberellin 3 | 0.1-5 |
| gibberellin 34 | 0.1-5 |
| gibberellin 44 | 0.1-5 |

After harvest of the microalgae from the culturing vessel, the microalgae is dried or dehydrated to form a composition of dried microalgae cells (i.e., reduced moisture content). The microalgae cells may be dried by at least one method selected from the group consisting of: freeze drying (or lypohilization), drum (or rotary) drying, spray drying, cross-flow air drying, solar drying, vacuum shelf drying, pulse combustion drying, flash drying, furnace drying, belt conveyor drying, and refractance window drying. In some embodiments, the microalgae cells may be dried by a combination of two or more methods, such as in a process with multiple drying methods in series. The process of drying the microalgae may reduce the percent moisture (on a wet basis) to the range of about 1-15% and result in a cake, flakes, or a powder, which is more uniform and more stable than the wet culture of microalgae. In some embodiments, the dried microalgae cells may be intact. In some embodiments, the dried microalgae cells may be lysed or disrupted. In some embodiments, the microalgae cells may be lysed or disrupted prior to or after drying by mechanical, electrical, acoustic, or chemical means. In some embodiments, drying the microalgae cells achieves an acceptable product stability for storage, with the reduction or elimination of chemical stabilizers. The composition may be stored in any suitable container such as, but not limited to, a bag, bucket, jug, tote, or bottle.

In some embodiments, the dried microalgae cells may have a moisture content of 1-15% on a wet basis. In some embodiments, the dried microalgae cells may have a moisture content of 1-2% on a wet basis. In some embodiments, the dried microalgae cells may have a moisture content of 2-3% on a wet basis. In some embodiments, the dried microalgae cells may have a moisture content of 3-5% on a wet basis. In some embodiments, the dried microalgae cells may have a moisture content of 5-7% on a wet basis. In some embodiments, the dried microalgae cells may have a moisture content of 7-10% on a wet basis. In some embodiments, the dried microalgae cells may have a moisture content of 10-12% on a wet basis. In some embodiments, the dried microalgae cells may have a moisture content of 12-15% on a wet basis. In some embodiments, the dried microalgae cells may have a moisture content of 1-8% on a wet basis. In some embodiments, the dried microalgae cells may have a moisture content of 8-15% on a wet basis.

The various drying processes may have different capabilities such as, but not limited to, the amount of moisture that may be removed, the preservation of metabolites (e.g., proteins, lipids, pigments, carbohydrates, polysaccharides, soluble nitrogen, phytohormones), and the effect on the cell wall or membrane. For example, loss of protein in *Spirulina* biomass has been found to increase proportionally as the drying temperature increases. Additionally, drying at high temperatures has been shown to alter polymer chains, alter interactions between polysaccharide and glycoprotein, and increase bound water content of polysaccharides. Pigments and fatty acids are also known to oxidize and de-stabilize to different degrees in different drying processes. The effectiveness of each drying method may also vary based on the microalgae species due to different physical characteristics of the microalgae (e.g., sheer sensitivity, cell size, cell wall thickness and composition). The method of drying and drying method parameters may also result in a structural change to the microalgae cell such as, but not limited to, increased porosity in the cell wall, changes in the cell wall make up or bonds, and measurable changes in cell characteristics (e.g., elasticity, viscosity, digestibility); as wells as functional differences when applied to plants that can be measured in changes in plant performance or plant characteristics. Drying microalgae with a combination of methods in series may also result in structural and functional changes, minimize structural and functional changes, or increase the effectiveness for a particular type of microalgae.

Drum drying comprises the use of sloped, rotating cylinders which use gravity to move the microalgal biomass from one end to the other. Drum drying may be conducted with direct contact between a hot gas and the microalgal biomass, or indirect heating in which the gas and microalgal biomass is separated by a barrier such as a steel shell. An example of a drum drying process for *Scenedesmus* may comprise 10 seconds of heating at 120° C. Possible effects to the microalga biomass in a drum drying process include sterilization of the biomass, and breaking of the cell wall. Microalgal biomass that is drum dried may have higher digestibility than microalgal biomass that is spray dried.

Freeze drying comprises freezing the microalgal biomass and then transferring the frozen biomass to a vacuum chamber with reduced pressure (e.g., 4.6 Torr). The ice in the microalgal biomass changes to vapor through sublimation which is collected on an extremely cold condenser and removed from the vacuum chamber. Freeze drying typically minimizes the degradation of unsaturated fatty acids and pigments (e.g., carotenoids) through oxidation, which preserves the nutritional value of the microalgal biomass. Although the targeted removal of water in the freeze drying process is beneficial, the process is very costly and time consuming which makes freeze drying impractical for many commercial applications. In some embodiments, microalgae dried by freeze drying may comprise 2-6% moisture (on a wet basis). An example of a freeze drying process for *Scenedesmus* may comprise 24 hours at −84° C. Freeze drying is known to maintain the integrity of the microalgal cell, but is also known been known in some cases to disrupt the cell or increase the pore size in the cell wall. In *Scenedesmus*, freeze drying was found to decrease rigidity, increase surface area by 165%, and increase pore size by 19% of the cells (see eSEM images below). In *Phaeodactylum ricornutum*, freeze drying had no effect on the total lipid content, made the cells more susceptible to lipolysis (i.e., breakdown of lipids, hydrolysis of triglycerides into glycerol and free fatty acids) upon storage than spray dried cells, and made the cells less susceptible to oxidation than spray dried cells.

Spray drying comprises atomizing an aqueous microalgae culture into droplets sprayed downwardly in a vertical tower through which hot gases pass downward. The gas stream may be exhausted through a cyclonic separator. The process of spray drying is expensive, but slightly cheaper than freeze drying. Spray drying has become the method of choice for high value products (>$1,000/ton). With the proper type of burner, oxygen can be virtually eliminated from the recycled drying gas, which prevents the oxidation of oxygen sensitive products (e.g., carotenoids). In some embodiments, microalgae dried by spray drying may comprise 1-7% moisture (on a wet basis). Examples of spray drying systems include: box dryers, tall-form spray dryers, fluidized bed dryers, and moving fluidized bed dryers (e.g., FilterMat spray dryer GEA Process Engineering Inc.). An open cycle spray dryer with a particular direct fired air heater may operate at elevated temperatures (e.g., 60-93° C.) and high oxygen concentrations (e.g., 19-20%). The possible effects of spray drying on microalgal biomass include rupturing the cells walls, reduction of protein content by 10-15%, significant deterioration of pigments (depending on the oxygen concentration), and a lower digestibility than drum drying. In *Phyaeodactylum ricornutum*, spray drying had no effect on the total lipid content, made the cells less susceptible to lipolysis than freeze drying, and made the cells more susceptible to oxidation than freeze drying (possibly due to the breakdown of protective carotenoids).

Crossflow air drying uses movement of heated air across a layer of microalgae on a tray, which is a modification of indirect solar and convection oven driers. Crossflow air drying is faster than solar drying, cheaper than drum drying, and is known to typically not break the microalgal cell wall. In some embodiments, microalgae dried by crossflow air drying may comprise 8-12% moisture (on a wet basis). Examples of crossflow air drying for *Spirulina* may comprise: 1) a temperature of 62° C. for 14 hours, 2) a temperature of 50-60° C., a relative humidity of 7-10%, an air velocity of 1.5 m/s, and a duration of 150-220 minutes, 3) a temperature of 40-60° C. and an air velocity of 1.9-3.8 m/s, and 4) temperatures of 50-70° C. for layers of 3-7 mm in a perforated tray with parallel air flow. Crossflow air drying of *Spirulina* has shown a loss in protein of about 17% and a loss in phycocyanin of 37-50%. Particularly, degradation of phycocyanin was found to occur above 60° C., but there was no significant change in the fatty acid composition in the crossflow air drying methods.

Examples of crossflow air drying of *Chlorella kessleri* and *Chlamydomonas reinhardtii* may comprise a temperature of 55° C. for more than 5 hours. Crossflow air drying of *Chlorella kessleri* and *Chlamydomonas reinhardtii* has produced a reduction of chlorophyll relative to the dry cell weight, an increase of total fatty acid content relative to the dry cell, a decrease of polar lipids relative to the dry cell weight, and a decrease in the availability of nutritional salts (e.g., S, N). A cell's sensitivity to air drying stress (as measured through the change in chlorophyll) may be correlated to the properties of the cell wall. For example, the crossflow air dried *Chlamydomonas reinhardtii* (hydroxyproline-rich glucoprotein based cell walls) had a larger decrease in chlorophyll than the *Chlorella kessleri* (sugar based cell walls), which may be associated with the cell wall's ability to restructure in S and N deficient conditions. In an example of drying 5-7 mm thick layers of *Aphanothece microscopia Nageli* at temperatures of 40-60° C. with parallel air flow of 1.5 m/s, it was found that drying conditions influenced the concentrations of protein, carbohydrates, and lipids in the biomass.

Solar drying methods may comprise the use of direct solar radiation to dry microalgae on sand or a plastic sheet, or the indirect use of solar radiation to heat air that is circulated around microalgae in a dryer. Direct solar drying is strongly weather dependent, slow, and may require a short duration of high heat (e.g., 120° C.) to increase the biological value of the microalgal biomass. An example of a direct solar drying process for *Scenedesmus* may comprise a 1,500 micron thickness white plastic drying bed liner, a temperature of 25-30° C., and a duration of 72 hours. The possible effects of direct solar drying on microalgal biomass include chlorophyll degradation, overheating of the biomass, and creation of an unpleasant odor. Indirect solar drying prevents overheating, has a higher drying rate than direct solar drying, but produces a less attractive profile in the final product. An indirect solar drying method for microalgae may comprise temperature of 65-70° C. for 0.5-6 hours.

Drying of a thin film of microalgal biomass in a convection oven is a fairly common practice performed in scientific literature to test the biomass going through further processing, but may be less practical for many commercial applications. Thin film convection oven drying has been demonstrated in the literature with species of *Chlorella*, *Chlamydomonas*, and *Scenedesmus*. In some embodiments, microalgae dried by oven drying may comprise 6-10% moisture (on a wet basis). Thin film convection oven drying methods may comprise temperatures of 30-90° C., and durations of 4-12 hours. Thin film convection oven dried microalgal biomass showed no significant change in the fatty acid profile and a slight decrease in the degree of unsaturation of fatty acids at higher temperature for ruptured cells (likely due to oxidation causing cleavage of unsaturated bonds).

Microalgae may be dried in thin layers with heat at a reduced pressure. Examples of drying of *Spirulina* in layers within a vacuum may comprise temperatures of 50-65° C. and a pressure of 0.05-0.06 atm. Possible effects on the microalgae that may result from vacuum shelf drying include development of a hygroscopic property (i.e., ability to attract and hold water particles from the surrounding environment by absorption or adsorption) and development of a porous structure.

Pulse combustion drying uses a blast of controlled heat to flash dry the microalgae. Air is pumped into a combustion chamber, mixed with a fuel and ignited to created pressurized hot gas (e.g., at 3 psi). The dryer may automatically blast the heated gas with quench air to control the temperature of the heated gas before coming into contact with the microalgae. The process is then repeated multiple times to provide the pulses of heated gas. Pulse combustion heating is known to dry microalgae at a low heat which preserves the integrity and nutritional value of the microalgae. Flash drying comprises spraying or injecting a mixture of dried and undried material into a hot gas stream, and is commonly used in wastewater sludge drying.

Drying of microalgae using an incinerator or furnace may comprise heating the biomass to a high temperature (e.g., 100° C.) to evaporate the water. The heating may be performed at a level below the temperature at which the microalgae will burn and may comprise using hot gases that proceed downwardly with the biomass in parallel flow. Microalgae that are dewatered to an appropriate solids level may be dried indirectly by heating elements lining the pathway of a belt conveyor. Refractance window drying is a dehydration method that uses infra-red light, rather than high direct temperature, to remove moisture from microalgae. Wet microalgae biomass may be translated through an evaporation chamber by a belt disposed above a circulating hot water reservoir to dry the microalgae with infra-red energy in a refractance window drying. In some embodiments, microalgae dried by refractance window drying may comprise 3-8% moisture (on a wet basis).

In some embodiments, the dry composition may be mixed with water and stabilized by heating and cooling in a pasteurization process, adjustment of pH, and the addition of an inhibitor of yeast and mold growth. In one non-limiting example of preparing the dried microalgae composition for application to plants, the microalgae harvested from the culturing system is first held in a harvest tank before centrifuging the culture. Once the microalgae is centrifuged, the centrifuge discharges the fraction rich in microalgae whole cell solids, but also containing the accompanying constituents from the culture medium, into a container at a temperature of about 30° C. The microalgae composition is then dried.

For a non-limiting embodiment where the dried microalgae is mixed with water to make a liquid composition, the dried microalgae composition may then be placed in a tank and heated to a temperature of about 60° C. for about 2 hours to begin the pasteurization process. The microalgae based composition may then be diluted to a whole cells solids concentration of about 10-11% by weight and cooled to about 40° C. to complete the pasteurization process. The pH of the microalgae based composition may then be adjusted to a pH of about 4 by mixing in an effective amount of phosphoric acid for stabilization purposes. About 0.3% potassium sorbate may then be mixed with the microalgae based composition for stabilization purposes. The resulting liquid composition may be transferred to containers of a desired size stored at 3-5° C. until shipped.

In some embodiments, the microalgae based composition can be heated to a temperature in the range of 50-90° C. In some embodiments, the microalgae based composition can be heated to a temperature in the range of 55-65° C. In some embodiments, the microalgae based composition can be heated to a temperature in the range of 58-62° C. In some embodiments, the microalgae based composition can be heated to a temperature in the range of 50-60° C. In some embodiments, the microalgae based composition can be heated to a temperature in the range of 60-70° C. In some embodiments, the microalgae based composition can be heated to a temperature in the range of 70-80° C. In some embodiments, the microalgae based composition can be heated to a temperature in the range of 80-90° C.

In some embodiments, the microalgae based composition can be heated for a time period in the range of 90-150 minutes. In some embodiments, the microalgae based composition can be heated for a time period in the range of 110-130 minutes. In some embodiments, the microalgae based composition can be heated for a time period in the range of 90-100 minutes. In some embodiments, the microalgae based composition can be heated for a time period in the range of 100-110 minutes. In some embodiments, the microalgae based composition can be heated for a time period in the range of 110-120 minutes. In some embodiments, the microalgae based composition can be heated for a time period in the range of 120-130 minutes. In some embodiments, the microalgae based composition can be heated for a time period in the range of 130-140 minutes. In some embodiments, the microalgae based composition can be heated for a time period in the range of 140-150 minutes.

In some embodiments, the microalgae based composition can be heated for a time period in the range of 15-360 minutes. In some embodiments, the microalgae based composition can be heated for a time period in the range of 15-30 minutes. In some embodiments, the microalgae based composition can be heated for a time period in the range of 30-60 minutes. In some embodiments, the microalgae based composition can be heated for a time period in the range of 60-120 minutes. In some embodiments, the microalgae based composition can be heated for a time period in the range of 120-180 minutes. In some embodiments, the microalgae based composition can be heated for a time period in the range of 180-360 minutes.

In some embodiments, the microalgae based composition can be cooled to a temperature in the range of 35-45° C. In some embodiments, the microalgae based composition can be cooled to a temperature in the range of 36-44° C. In some embodiments, the microalgae based composition can be cooled to a temperature in the range of 37-43° C. In some embodiments, the microalgae based composition can be cooled to a temperature in the range of 38-42° C. In some embodiments, the microalgae based composition can be cooled to a temperature in the range of 39-41° C. In some embodiments, the microalgae based composition can be cooled to a temperature suitable for further processing or handling.

In some embodiments, the pH of the microalgae based composition can be adjusted downward to a pH in the range of 3-5. In some embodiments, the pH of the microalgae based composition can be adjusted upward to a pH in the range of 3-5. In some embodiments, the pH of the microalgae based composition can be adjusted to a pH in the range of 3.5-4.5. In some embodiments, the pH of the microalgae based composition can be adjusted to a pH in the range of 3-3.5. In some embodiments, the pH of the microalgae based composition can be adjusted to a pH in the range of 3.5-4. In some embodiments, the pH of the microalgae based composition can be adjusted to a pH in the range of 4-4.5. In some embodiments, the pH of the microalgae based composition can be adjusted to a pH in the range of 4.5-5.

In some embodiments, stabilizing means that are not active regarding the improvement of plant germination, emergence, and maturation, but instead aid in stabilizing the microalgae based composition can be added to prevent the proliferation of unwanted microorganisms (e.g., yeast, mold) and prolong shelf life. Such inactive but stabilizing means can comprise an acid, and a yeast and mold inhibitor. In some embodiments, the stabilizing means are suitable for plants and do not inhibit the growth or health of the plant. In the alternative, the stabilizing means can contribute to nutritional properties of the liquid composition, such as but not limited to, the levels of nitrogen, phosphorus, or potassium.

In some embodiment, the composition may be stabilized with a culture stabilizer selected from: potassium sorbate, phosphoric acid, ascorbic acid, sodium benzoate, citric acid, other acids with similar stabilization properties, and any combination thereof. In some embodiments, the step of adjusting the pH of the composition comprises contacting the composition with stabilizing means comprising an acid. In some embodiments, such an acid can comprise phosphoric acid ($H_3PO_4$). In some embodiments, the amount of acid needed to adjust the pH can comprise different amounts of acid depending on the starting pH of the microalgae composition, which can vary based on culturing conditions of the microalgae, residual concentrations of organic carbon or other nutrients, and previous processing of the composition. In some embodiments, the microalgae based composition can comprise less than 0.3% phosphoric acid or an acid with similar stabilization properties. In some embodiments, the microalgae based composition can comprise 0.01-0.3% phosphoric acid or an acid with similar stabilization properties. In some embodiments, the microalgae based composition can comprise 0.05-0.25% phosphoric acid or an acid with similar stabilization properties. In some embodiments, the microalgae based composition can comprise 0.01-0.1% phosphoric acid or an acid with similar stabilization properties. In some embodiments, the microalgae based composition can comprise 0.1-0.2% phosphoric acid or an acid with similar stabilization properties. In some embodiments, the microalgae based composition can comprise 0.2-0.3% phosphoric acid or an acid with similar stabilization properties.

In some embodiments, the yeast and mold inhibitor can comprise potassium sorbate ($C_6H_7KO_2$). In some embodiments, the composition can comprise less than 0.5% potassium sorbate. In some embodiments, the composition can comprise 0.01-0.5% potassium sorbate. In some embodiments, the composition can comprise 0.05-0.4% potassium sorbate. In some embodiments, the composition can comprise 0.01-0.1% potassium sorbate. In some embodiments, the composition can comprise 0.1-0.2% potassium sorbate. In some embodiments, the composition can comprise 0.2-0.3% potassium sorbate. In some embodiments, the composition can comprise 0.3-0.4% potassium sorbate. In some embodiments, the composition can comprise 0.4-0.5% potassium sorbate.

In some embodiments, a method of preparing a low concentration mixotrophic *Chlorella* based liquid composition for application to plants can comprise: culturing *Chlorella* in an liquid culture medium and mixotrophic conditions comprising utilization of an organic carbon source and photosynthetically active radiation as energy sources in a culturing vessel; harvesting the mixotrophic *Chlorella* culture from the culturing vessel; drying the mixotrophic *Chlorella* culture; and mixing the dried mixotrophic *Chlorella* culture with water, and an acid and a yeast and mold inhibitor to form a composition with a concentration of an effective amount of the mixotrophic *Chlorella* based composition for application to a plant for enhanced characteristics.

In some embodiments, a method of preparing a dried microalgae based liquid composition for application to plants can comprise: heating a composition comprising water and dried microalgae cells in an liquid medium at a temperature in the range of 50-70° C.; adjusting concentration of the dried cells in the heated composition to a concentration in the range of 5-30% dried microalgae cells by weight; cooling the composition to a temperature in the range of 35-45° C.; adjusting the pH of the composition to a pH in the range of 3-5; and contacting the composition with a yeast and mold inhibitor.

In some embodiments, the composition can comprise 1-20% solids by weight of dried microalgae cells. In some embodiments, the composition can comprise 1-5% solids by weight of dried microalgae cells. In some embodiments, the composition can comprise 1-2% solids by weight of dried microalgae cells. In some embodiments, the composition can comprise 2-3% solids by weight of dried microalgae cells. In some embodiments, the composition can comprise 3-5% solids by weight of dried microalgae cells. In some embodiments, the composition can comprise 5-10% solids by weight of dried microalgae cells. In some embodiments, the composition can comprise 10-15% solids by weight of dried microalgae cells. In some embodiments, the composition can comprise 15-20% solids by weight of dried microalgae cells. In some embodiments, further dilution of the dried microalgae cells percent solids by weight can be occur before application for low concentration applications of the composition.

The composition can be diluted to a lower concentration for an effective amount in a soil or foliar application by mixing a volume of the composition in a volume of water. The percent solids of dried microalgae cells resulting in the diluted composition can be calculated by multiplying the original percent solids of dried microalgae cells in the composition by the ratio of the volume of the composition to the volume of water.

In some embodiments, the composition can comprise less than 1% solids by weight of dried microalgae cells. In some embodiments, the composition can comprise less than 0.9% solids by weight of dried microalgae cells. In some embodiments, the composition can comprise less than 0.8% solids by weight of dried microalgae cells. In some embodiments, the composition can comprise less than 0.7% solids by weight of dried microalgae cells. In some embodiments, the composition can comprise less than 0.6% solids by weight of dried microalgae cells. In some embodiments, the composition can comprise less than 0.5% solids by weight of dried microalgae cells. In some embodiments, the composition can comprise less than 0.4% solids by weight of dried microalgae cells. In some embodiments, the composition can comprise less than 0.3% solids by weight of dried microalgae cells. In some embodiments, the composition can comprise less than 0.2% solids by weight of dried microalgae cells. In some embodiments, the composition can comprise less than 0.1% solids by weight of dried microalgae cells. In some embodiments, the composition can comprise less than 0.1-1% solids by weight of dried microalgae cells.

In some embodiments, the composition can comprise low concentrations of bacteria contributing to the solids percentage of the composition in addition to the dried microalgae cells. Examples of bacteria found in non-axenic mixotrophic conditions can be found in WO2014/074769A2 (Ganuza, et al.), hereby incorporated by reference. A live bacteria count can be determined using methods known in the art such as plate counts, plate counts using Petrifilm available from 3M (St. Paul, Minn.), spectrophotometric (turbidimetric) measurements, visual comparison of turbidity with a known standard, direct cell counts under a microscope, cell mass determination, and measurement of cellular activity. Live bacteria counts in a non-axenic mixotrophic microalgae culture can range from $10^4$ to $10^9$ CFU/mL, and can depend on contamination control measures taken during the culturing of the microalgae. The level of bacteria in the composition can be determined by an aerobic plate count which quantifies aerobic colony forming units (CFU) in a designated volume. In some embodiments, the composition comprises an aerobic plate count of 40,000-400,000 CFU/mL. In some embodiments, the composition comprises an aerobic plate count of 40,000-100,000 CFU/mL. In some embodiments, the composition comprises an aerobic plate count of 100,000-200,000 CFU/mL. In some embodiments, the composition comprises an aerobic plate count of 200,000-300,000 CFU/mL. In some embodiments, the composition comprises an aerobic plate count of 300,000-400,000 CFU/mL.

In some embodiments, the composition with added water can comprise 70-95% water. In some embodiments, the composition with added water can comprise 85-95% water. In some embodiments, the composition with added water can comprise 70-75% water. In some embodiments, the composition can comprise 75-80% water. In some embodiments, the composition with added water can comprise 80-85% water. In some embodiments, the composition can comprise 85-90% water. In some embodiments, the composition with added water can comprise 90-95% water. The addition of water to the composition facilitates administration of the composition in a variety of manners, such as but not limited to: flowing through an irrigation system, flowing through an above ground drip irrigation system, flowing through a buried drip irrigation system, flowing through a central pivot irrigation system, sprayers, sprinklers, water cans, and the like.

The microalgae based composition can be used immediately after formulation, or can be stored in containers for later use. In some embodiments, the microalgae based composition can be stored out of direct sunlight. In some embodiments, the microalgae based composition can be refrigerated. In some embodiments, the microalgae based composition can be stored at 1-10° C. In some embodiments, the microalgae based composition can be stored at 1-3° C. In some embodiments, the microalgae based composition can be stored at 3-5° C. In some embodiments, the microalgae based composition can be stored at 5-8° C. In some embodiments, the composition can be stored at 8-10° C.

Administration of the dried microalgae composition treatment to a seed or plant can be in an amount effective to produce an enhanced characteristic in the plant compared to a substantially identical population of untreated plant. Such enhanced characteristics can comprise accelerated seed germination, improved seedling vigor, accelerated seedling emergence, improved seedling emergence, improved leaf formation, accelerated leaf formation, improved plant maturation, accelerated plant maturation, increased plant yield, increased plant growth, increased plant quality, increased plant health, increased flowering, increased fruit yield, increased fruit growth, and increased fruit quality. Non-limiting examples of such enhanced characteristics can comprise accelerated achievement of the hypocotyl stage, accelerated protrusion of a stem from the soil, accelerated achievement of the cotyledon stage, accelerated leaf formation, increased leaf size, increased leaf area index, increased marketable plant weight, increased marketable plant yield, increased marketable fruit weight, increased production plant weight, increased production fruit weight, increased utilization (indicator of efficiency in the agricultural process based on ratio of marketable fruit to unmarketable fruit), increased chlorophyll content (indicator of plant health), increased plant weight (indicator of plant health), increased root weight (indicator of plant health), increased root mass (indicator of plant health), increased shoot weight (indicator of plant health), increased plant height, increased thatch height, increased resistance to salt stress, increased plant resistance to heat stress, increased plant resistance to heavy metal stress, increased plant resistance to drought, improved color, reduced insect damage, reduced blossom end rot, and reduced sun burn. Such enhanced characteristics can occur individually in a plant, or in combinations of multiple enhanced characteristics. The characteristic of flowering has is important for not only the ornamental market, but also for fruiting plants where an increase in flowering may correlate to an increase in fruit production.

Seed Coating

In one non-limiting embodiment, the administration of the dried microalgae composition treatment can comprise coating a seed. In some embodiments, a seed may be coated by passing through a slurry comprising microalgae and then dried. In some embodiments, the seed may be coated with the dried microalgae composition and other components such as, but not limited to, binders and fillers known in the art to be suitable for coating seeds. The fillers may comprise suitable inorganic particles such as, but not limited to, silicate particles, carbonate particles, and sulphate particles, quartz, zeolites, pumice, perlite, diatomaceous earth, pyrogene silica, $Sb_2O_3$, $TiO_2$, lithopone, ZnO, and hydrated aluminum oxide. The binders may include, but are not limited to, water-souble polymers, polyvinyl acetate, polyvinyl alcohol, polyvinyl pyrrolidone, polyurethane, methyl cellulose, carboxymethyl cellulose, hydroxylpropyl cellulose, sodium alginate, polyacrylate, casein, gelatin, pullulan, polyacrylamide, polyethylene oxide, polystyrene, styrene acrylic copolymers, styrene butadiene polymers, poly (N-vinylacetamide), waxes, canauba wax, paraffin wax, polyethylene wax, bees wax, polypropylene wax, and ethylene vinyl acetate. In some embodiments, the seed coating may comprise a wetting and dispersing additive such as, but not limited to polyacrylates, organo-modified polyacrylates, sodium polyacrylates, polyurethanes, phosphoric acid esters, star polymers, and modified polyethers.

In some embodiments, the seed coating may comprise other components such as, but not limited to, a solvent, thickener, colouring agent, anti-foaming agent, biocide, surfactant, and pigment. In some embodiments, the seed coating may comprise a hydrogel or film coating materials. In some embodiments, the concentration of dried microalgae in the seed coating may comprise 0.1-20% solids. In some embodiments, the concentration of microalgae in the seed coating may comprise less than 0.1% solids. In some embodiments, the concentration of dried microalgae in the seed coating may comprise 0.1-1% solids. In some embodiments, the concentration of dried microalgae in the seed coating may comprise 1-2% solids. In some embodiments, the concentration of dried microalgae in the seed coating may comprise 2-3% solids. In some embodiments, the concentration of dried microalgae in the seed coating may comprise 3-5% solids. In some embodiments, the concentration of dried microalgae in the seed coating may comprise 5-10% solids. In some embodiments, the concentration of dried microalgae in the seed coating may comprise 10-15% solids. In some embodiments, the concentration of dried microalgae in the seed coating may comprise 15-20% solids. In some embodiments, the seed may be coated in single step. In some embodiments, the seed may be coated in multiple steps. Conventional or otherwise suitable coating equipment or techniques may be used to coat the seeds. Suitable equipment may include drum coaters, fluidized beds, rotary coaters, side vended pan, tumble mixers, and spouted beds. Suitable techniques may comprise mixing in a container, tumbling, spraying, or immersion. After coating, the seeds may be dried or partially dried.

Seed Soak Application

In one non-limiting embodiment, the administration of the dried microalgae composition treatment can comprise soaking the seed in an effective amount of the composition mixed with water (aqueous mixed composition) before planting the seed. In some embodiments, the administration of the dried microalgae composition further comprises removing the seed from the aqueous mixed composition after soaking, and drying the seed before planting. In some embodiments, the seed can be soaked in the aqueous mixed composition for a time period in the range of 90-150 minutes. In some embodiments, the seed can be soaked in the aqueous mixed composition for a time period in the range of 110-130 minutes. In some embodiments, the seed can be soaked in the aqueous mixed composition for a time period in the range of 90-100 minutes. In some embodiments, the seed can be soaked in the aqueous mixed composition for a time period in the range of 100-110 minutes. In some embodiments, the seed can be soaked in the aqueous mixed composition for a time period in the range of 110-120 minutes. In some embodiments, the seed can be soaked in the aqueous mixed composition for a time period in the range of 120-130 minutes. In some embodiments, the seed can be soaked in the aqueous mixed composition for a time period in the range of 130-140 minutes. In some embodiments, the seed can be soaked in the aqueous mixed composition for a time period in the range of 140-150 minutes. In some embodiments, the seed can be soaked in the aqueous mixed composition for a time period up to 3 hours, 4 hours, 5 hours, 6 hours, 7 hours, 8 hours, 9 hours, or 10 hours.

In some embodiments, the effective amount in a seed soak application of the dried microalgae composition can comprise a concentration in the range of 0.007925-0.079252% (e.g., about 0.008% to about 0.080%) solids. In some embodiments, the effective amount in a seed soak application of the dried microalgae composition can comprise a concentration in the range 0.009245-0.071327% (e.g., about 0.009% to about 0.070%) solids. In some embodiments, the effective amount in a seed soak application of the dried microalgae composition can comprise a concentration in the range of 0.007925-0.05547% (e.g., about 0.008% to about 0.055%) solids. In some embodiments, the effective amount in a seed soak application of the dried microalgae composition can comprise a concentration in the range 0.009246-0.063401% (e.g., about 0.009% to about 0.065%) solids. In some embodiments, the effective amount in a seed soak application of the dried microalgae composition can comprise a concentration in the range of 0.010567-0.071327% (e.g., about 0.010% to about 0.070%) solids. In some embodiments, the effective amount in a seed soak application of the dried microalgae composition can comprise a concentration in the range of 0.011888-0.079252% (e.g., about 0.012% to about 0.080%) solids.

In some embodiments, the concentration of dried microalgae in the seed soak application may comprise 0.1-1% solids. In some embodiments, the concentration of dried microalgae in the seed soak application may comprise 1-2% solids. In some embodiments, the concentration of dried microalgae in the seed soak application may comprise 2-3% solids. In some embodiments, the concentration of dried microalgae in the seed soak application may comprise 3-5% solids. In some embodiments, the concentration of dried microalgae in the seed soak application may comprise 5-10% solids. In some embodiments, the concentration of dried microalgae in the seed soak application may comprise 10-15% solids. In some embodiments, the concentration of dried microalgae in the seed soak application may comprise 15-20% solids.

Soil Application

In another non-limiting embodiment, the administration of the dried microalgae composition treatment can comprise mixing an effective amount of the composition with a solid growth medium, such as soil, potting mix, compost, or inert hydroponic material, prior to planting a seed, seedling, or plant in the solid growth medium. The dried microalgae composition may be mixed in the solid growth medium at an inclusion level of 0.1-20% by volume. In some embodiments, the effective amount in a mixed solid growth medium application of the dried microalgae composition can comprise a concentration in the range of 0.1-1% solids. In some embodiments, the effective amount in a mixed solid growth medium application of the dried microalgae composition can comprise a concentration in the range of 1-3%% solids. In some embodiments, the effective amount in a mixed solid growth medium application of the dried microalgae composition can comprise a concentration in the range of 3-5% solids. In some embodiments, the effective amount in a mixed solid growth medium application of the dried microalgae composition can comprise a concentration in the range of 5-10% solids. In some embodiments, the effective amount in a mixed solid growth medium application of the dried microalgae composition can comprise a concentration in the range of 10-20% solids.

In another non-limiting embodiment, the administration of the dried microalgae composition treatment can comprise contacting the soil in the immediate vicinity of the planted seed or plant with an effective amount of the liquid composition. In some embodiments, the dried microalgae composition can be mixed with water and supplied to the soil by injection into a low volume irrigation system, such as but not limited to a drip irrigation system supplying water beneath the soil through perforated conduits or at the soil level by fluid conduits hanging above the ground or protruding from the ground. In some embodiments, the dried composition can be mixed with water and supplied to the soil by a soil drench method wherein the aqueous mixed composition is poured on the soil.

In some embodiments, the effective amount in a soil application of the dried microalgae composition can comprise a concentration in the range of 0.001321-0.396258% (e.g., about 0.001% to about 0.400%) solids. In some embodiments, the effective amount in a soil application of the dried microalgae composition can comprise a concentration in the range of 0.001321-0.079252% (e.g., about 0.001% to about 0.080%) solids. In some embodiments, the effective amount in a soil application of the dried microalgae composition can comprise a concentration in the range 0.002642-0.055476% (e.g., about 0.003% to about 0.055%) solids. In some embodiments, the effective amount in a soil application of the dried microalgae composition can comprise a concentration in the range of 0.013201-0.158503% (e.g., about 0.013% to about 0.160%) solids. In some embodiments, the effective amount in a soil application of the dried microalgae composition can comprise a concentration in the range of 0.026417-0.237755% (e.g., about 0.025% to about 0.250%) solids. In some embodiments, the effective amount in a soil application of the dried microalgae composition can comprise a concentration in the range of 0.039626-0.356631% (e.g., about 0.040% to about 0.360%) solids. In some embodiments, the effective amount in a soil application of the dried microalgae composition can comprise a concentration in the range of 0.039626-0.317007% (e.g., about 0.040% to about 0.320%) solids. In some embodiments, the effective amount in a soil application of the dried microalgae composition can comprise a concentration in the range of 0.052834-0.396258% (e.g., about 0.055% to about 0.400%) solids.

In some embodiments, the dried microalgae composition is applied to the soil once. In some embodiments, the dried microalgae composition is applied to the soil multiple times. The frequency of the application of the dried microalgae composition can be expressed as the number of applications per period of time (e.g., two applications per month), or by the period of time between applications (e.g., one application every 21 days). In some embodiments, the plant can be contacted by the dried microalgae composition in a soil application every 3-28 days. In some embodiments, the plant can be contacted by the dried microalgae composition in a soil application every 4-10 days. In some embodiments, the plant can be contacted by the dried microalgae composition in a soil application every 18-24 days. In some embodiments, the plant can be contacted by the dried microalgae composition in a soil application every 3-7 days. In some embodiments, the plant can be contacted by the dried microalgae composition in a soil application every 7-14 days. In some embodiments, the plant can be contacted by the dried microalgae composition in a soil application every 14-21 days. In some embodiments, the plant can be contacted by the dried microalgae composition in a soil application every 21-28 days.

Soil application(s) of the dried microalgae composition generally begin after the plant has become established, but can begin before establishment, at defined time period after planting, or at a defined time period after emergence form the soil in some embodiments. In some embodiments, the plant can be first contacted by the dried microalgae composition in a soil application 5-14 days after the plant emerges from the soil. In some embodiments, the plant can be first contacted by dried microalgae composition in a soil application 5-7 days after the plant emerges from the soil. In some embodiments, the plant can be first contacted by the dried microalgae composition in a soil application 7-10 days after the plant emerges from the soil. In some embodiments, the plant can be first contacted by the dried microalgae composition in a soil application 10-12 days after the plant emerges from the soil. In some embodiments, the plant can be first contacted by dried microalgae composition in a soil application 12-14 days after the plant emerges from the soil.

Capillary Action Application

In another non-limiting embodiment, the administration of the dried microalgae based composition treatment can comprise mixing the dried microalgae with water to form an aqueous mixed composition, first soaking the seed in water, removing the seed from the water, drying the seed, applying an effective amount of the aqueous mixed composition below the seed planting level in the soil, and planting the seed, wherein the composition supplied to the seed from below by capillary action. In some embodiments, the seed can be soaked in water for a time period in the range of 90-150 minutes. In some embodiments, the seed can be soaked in water for a time period in the range of 110-130 minutes. In some embodiments, the seed can be soaked in water for a time period in the range of 90-100 minutes. In some embodiments, the seed can be soaked in water for a time period in the range of 100-110 minutes. In some embodiments, the seed can be soaked in water for a time period in the range of 110-120 minutes. In some embodiments, the seed can be soaked in water for a time period in the range of 120-130 minutes. In some embodiments, the seed can be soaked in water for a time period in the range of 130-140 minutes. In some embodiments, the seed can be soaked in water for a time period in the range of 140-150 minutes.

In some embodiments, the effective amount in a capillary action application of the dried microalgae composition can comprise a concentration in the range of 0.007925-0.079252% (e.g., about 0.008% to about 0.080%) solids. In some embodiments, the effective amount in a capillary action application of the dried microalgae composition can comprise a concentration in the range of 0.009245-0.071327% (e.g., about 0.009% to about 0.075%) solids. In some embodiments, the effective amount in a capillary action application of the dried microalgae composition can comprise a concentration in the range of 0.007925-0.05547% (e.g., about 0.008% to about 0.055%) solids. In some embodiments, the effective amount in a capillary action application of the dried microalgae composition can comprise a concentration in the range of 0.009246-0.063401% (e.g., about 0.009% to about 0.065%) solids. In some embodiments, the effective amount in a capillary action application of the dried microalgae composition can comprise a concentration in the range of 0.010567-0.071327% (e.g., about 0.010% to about 0.075%) solids. In some embodiments, the effective amount in a capillary action application of the dried microalgae composition can comprise a concentration in the range of 0.011888-0.079252% (e.g., about 0.012% to about 0.080%) solids.

In some embodiments, the concentration of dried microalgae in the capillary action application may comprise 0.1-1% solids. In some embodiments, the concentration of dried microalgae in capillary action application may comprise 1-2% solids. In some embodiments, the concentration of dried microalgae in the capillary action application may comprise 2-3% solids. In some embodiments, the concentration of dried microalgae in the capillary action application may comprise 3-5% solids. In some embodiments, the concentration of dried microalgae in the capillary action application may comprise 5-10% solids. In some embodiments, the concentration of dried microalgae in the capillary action application may comprise 10-15% solids. In some embodiments, the concentration of dried microalgae in the capillary action application may comprise 15-20% solids.

Foliar Application

In one non-limiting embodiment, the administration of the dried microalgae composition treatment can comprise mixing the dried microalgae with water to form an aqueous mixed composition and contacting the foliage of the plant with an effective amount of the composition. In some embodiments, the composition can be sprayed on the foliage by a hand sprayer, a sprayer on an agriculture implement, a sprinkler, a broad distribution system such as a crop duster, or the like.

In some embodiments, the effective amount in a foliar application of the dried microalgae composition can comprise a concentration in the range of 0.002642-0.079252% (e.g., about 0.003% to about 0.080%) solids. In some embodiments, the effective amount in a foliar application of dried microalgae composition can comprise a concentration in the range of 0.002642-0.023775% (e.g., about 0.003% to about 0.025%) solids. In some embodiments, the effective amount in a foliar application of the dried microalgae composition can comprise a concentration in the range of 0.003963-0.031701% (e.g., about 0.004% to about 0.035%) solids. In some embodiments, the effective amount in a foliar application of composition can comprise a concentration in the range of 0.005283-0.039626% (e.g., about 0.005% to about 0.040%) solids. In some embodiments, the effective amount in a foliar application of the dried microalgae composition can comprise a concentration in the range of 0.006604-0.047551% (e.g., about 0.007% to about 0.050%) solids. In some embodiments, the effective amount in a foliar application of the dried microalgae composition can comprise a concentration in the range 0.007925-0.055476% (e.g., about 0.008% to about 0.055%) solids. In some embodiments, the effective amount in a foliar application of the dried microalgae composition can comprise a concentration in the range of 0.009246-0.063401% (e.g., about 0.009% to about 0.065%) solids. In some embodiments, the effective amount in a foliar application of the dried microalgae composition can comprise a concentration in the range of 0.010567-0.071327% (e.g., about 0.010% to about 0.070%) solids. In some embodiments, the effective amount in a foliar application of the dried microalgae composition can comprise a concentration in the range of 0.011888-0.079252% (e.g., about 0.012% to about 0.080%) solids.

In some embodiments, the concentration of dried microalgae in the foliar application may comprise 0.1-1% solids. In some embodiments, the concentration of dried microalgae in foliar application may comprise 1-2% solids. In some embodiments, the concentration of dried microalgae in the foliar application may comprise 2-3% solids. In some embodiments, the concentration of dried microalgae in the foliar application may comprise 3-5% solids. In some embodiments, the concentration of dried microalgae in the foliar application may comprise 5-10% solids. In some embodiments, the concentration of dried microalgae in the foliar application may comprise 10-15% solids. In some embodiments, the concentration of dried microalgae in the foliar application may comprise 15-20% solids.

The frequency of the application of the dried microalgae composition can be expressed as the number of applications per period of time (e.g., two applications per month), or by the period of time between applications (e.g., one application every 21 days). In some embodiments, the plant can be contacted by the dried microalgae composition in a foliar application every 3-28 days, or more. In some embodiments, the plant can be contacted by the dried microalgae composition in a foliar application every 4-10 days. In some embodiments, the plant can be contacted by dried microalgae composition in a foliar application every 18-24 days. In some embodiments, the plant can be contacted by dried microalgae composition in a foliar application every 3-7 days. In some embodiments, the plant can be contacted by the dried microalgae composition in a foliar application every 7-14 days. In some embodiments, the plant can be contacted by the dried microalgae composition in a foliar application every 14-21 days. In some embodiments, the plant can be contacted by the dried microalgae composition in a foliar application every 21-28 days.

Foliar application(s) of the dried microalgae composition generally begin after the plant has become established, but can begin before establishment, at defined time period after planting, or at a defined time period after emergence form the soil in some embodiments. In some embodiments, the plant can be first contacted by the dried microalgae composition in a foliar application 5-14 days after the plant emerges from the soil. In some embodiments, the plant can be first contacted by the dried microalgae composition in a foliar application 5-7 days after the plant emerges from the soil. In some embodiments, the plant can be first contacted by the dried microalgae composition in a foliar application 7-10 days after the plant emerges from the soil. In some embodiments, the plant can be first contacted by the dried microalgae composition in a foliar application 10-12 days after the plant emerges from the soil. In some embodiments, the plant can be first contacted by the dried microalgae composition in a foliar application 12-14 days after the plant emerges from the soil.

Hydroponic Application

In another non-limiting embodiment, the administration of the dried microalgae composition to a seed or plant can comprise mixing the dried microalgae with water or a liquid nutrient medium and applying the composition in combination with a nutrient medium to seeds disposed in and plants growing in a hydroponic growth medium or an inert growth medium (e.g., coconut husks). The dried microalgae composition can be applied once, multiple times per day, multiple times per week, or multiple times per growing season.

In some embodiments, the concentration of dried microalgae in the hydroponic application may comprise 0.1-1% solids. In some embodiments, the concentration of dried microalgae in hydroponic application may comprise 1-2% solids. In some embodiments, the concentration of dried microalgae in the hydroponic application may comprise 2-3% solids. In some embodiments, the concentration of dried microalgae in the hydroponic application may comprise 3-5% solids. In some embodiments, the concentration of dried microalgae in the hydroponic application may comprise 5-10% solids. In some embodiments, the concentration of dried microalgae in the hydroponic application may comprise 10-15% solids. In some embodiments, the concentration of dried microalgae in the hydroponic application may comprise 15-20% solids.

EXAMPLES

Embodiments of the invention are exemplified and additional embodiments are disclosed in further detail in the following examples, which are not in any way intended to limit the scope of any aspect of the invention described herein. The strain of *Chlorella* used in the following examples provides an exemplary embodiment of the invention but is not intended to limit the invention to a particular strain of microalgae. Analysis of the DNA sequence of the exemplary strain of *Chlorella* in the NCBI 18s rDNA reference database at the Culture Collection of Algae at the University of Cologne (CCAC) showed substantial similarity (i.e., greater than 95%) with multiple known strains of *Chlorella* and *Micractinium*. Those of skill in the art will recognize that *Chlorella* and *Micractinium* appear closely related in many taxonomic classification trees for microalgae, and strains and species may be re-classified from time to time. While the exemplary microalgae strain is referred to in the instant specification as *Chlorella*, it is recognized that microalgae strains in related taxonomic classifications with similar characteristics to the exemplary microalgae strain would reasonably be expected to produce similar results.

Example 1

Samples of mixotrophic *Chlorella* whole cells were analyzed by the National Research Council Canada (Ottawa, Ontario) for phytohormone content. All mixotrophic *Chlorella* whole cell samples had to be dried for analysis, and the results are reported with respect to dry weight (DW). Two samples of mixotrophic *Chlorella* whole cells analyzed contained mixotrophic *Chlorella* which had been dried by a drum drier prior to analysis, consisting of one sample where the mixotrophic *Chlorella* whole cells had been previously stored in a freezer (stored) and one sample where the mixotrophic *Chlorella* whole cells had not been previously stored (fresh). A sample of mixotrophic *Chlorella* whole cells which was freeze dried before analysis was used as the closest approximation of the content of mixotrophic *Chlorella* cells that have not been subjected to a drying process.

The results of the sample analysis are shown in Tables 4-7, with n.d. indicating where the metabolite was not detected. The reported ng/g is equivalent to parts per billion (ppb) levels.

TABLE 4

| Solid Sample | ABA and ABA metabolites (ng/g DW) | | | | |
| --- | --- | --- | --- | --- | --- |
| | ABA | ABAGE | PA | Neo-PA | t-ABA |
| Mixotrophic *Chlorella* sp. - drum dried (stored) | 8 | n.d | n.d | <3.9 | 11 |
| Mixotrophic *Chlorella* sp. - Drum Dried (fresh) | <3.9 | <3.9 | <3.9 | n.d. | <3.9 |
| Mixotrophic *Chlorella* sp. - Freeze Dried (stored) | 11 | <3.9 | 7 | <3.9 | 15 |

The phytohormones in Table 4 are abbreviated as follows: ABA=cis-Abscisic acid; ABAGE=Abscisic acid glucose ester; PA=Phaseic acid; Neo-PA=Neo-Phaseic acid; and t-ABA=trans-Abscisic acid. As shown in Table 4, both drum dried samples showed lower levels of ABA and ABA metabolites than the freeze dried sample.

TABLE 5

| Solid Sample | Cytokinins (ng/g DW) | | | | | | | |
| --- | --- | --- | --- | --- | --- | --- | --- | --- |
| | t-ZOG | t-Z | c-Z | t-ZR | c-ZR | dhZR | iP | iPR |
| Mixotrophic *Chlorella* sp. - drum dried (stored) | n.d. | <1.3 | 7 | 17 | 238 | n.d. | 3 | 13 |
| Mixotrophic *Chlorella* sp. - Drum Dried (fresh) | n.d. | n.d. | <1.2 | 6 | 233 | 1 | <1 | 4 |
| Mixotrophic *Chlorella* sp. - Freeze Dried (stored) | n.d. | 3 | 14 | 11 | 42 | <1 | 6 | 3 |

The phytohormones in Table 5 are abbreviated as follows: t-ZOG=(trans) Zeatin-O-glucoside; t-Z=(trans) Zeatin; c-Z=(cis) Zeatin; t-ZR=(trans) Zeatin riboside; c-ZR=(cis) Zeatin riboside; dhZR=Dihydrozeatin riboside; iP=Isopentenyladenine; and iPR=Isopentenyladenosine. As shown in Table 5, both drum dried samples showed lower levels of t-Z, c-Z, and iP than the freeze dried sample. The composition samples showed detectable levels of t-ZOG, c-Z, c-ZR, iP, and iPR, indicating that subjecting the mixotrophic *Chlorella* based composition to a drum drying process may reduce the c-Z and iP content of the composition.

TABLE 6

| Solid Sample | Auxins (ng/g DW) | | | | |
| --- | --- | --- | --- | --- | --- |
| | IAA | IAA-Ala | IAA-Asp | IAA-Glu | IAA-Leu |
| Mixotrophic *Chlorella* sp. - drum dried (stored) | 412 | n.d. | n.d. | n.d. | n.d. |
| Mixotrophic *Chlorella* sp. - Drum Dried (fresh) | 414 | <3.9 | n.d. | n.d. | n.d. |
| Mixotrophic *Chlorella* sp. - Freeze Dried (stored) | 794 | n.d. | n.d. | n.d. | n.d. |

The phytohormones in Table 6 are abbreviated as follows IAA=Indole-3-acetic acid; IAA-Ala=N-(Indole-3-yl-acetyl)-alanine; IAA-Asp=N-(Indole-3-yl-acetyl)-aspartic acid; IAA-Glu=N-(Indole-3-yl-acetyl)-glutamic acid; and IAA-Leu=N-(Indole-3-yl-acetyl)-leucine. As shown in Table 6, both drum dried samples showed lower levels of IAA than the freeze dried sample.

TABLE 7

| Solid Sample | Gibberellins (ng/g DW) | | | | | | | |
|---|---|---|---|---|---|---|---|---|
| | GA3 | GA4 | GA7 | GA8 | GA34 | GA44 | GA51 | GA53 |
| Mixotrophic *Chlorella* sp. - drum dried (stored) | <3.9 | n.d. | n.d. | n.d. | n.d. | n.d. | n.d. | n.d. |
| Mixotrophic *Chlorella* sp. - Drum Dried (fresh) | <3.9 | n.d. | n.d. | n.d. | n.d. | <3.9 | n.d. | n.d. |
| Mixotrophic *Chlorella* sp. - Freeze Dried (stored) | 7 | n.d. | n.d. | n.d. | <3.9 | n.d. | n.d. | n.d. |

The phytohormones in Table 7 are abbreviated as follows: GA=Gibberellins. As shown in Table 7, both drum dried samples showed lower levels of GA3 than the freeze dried sample.

Example 2

Samples of mixotrophic *Chlorella* whole cells were analyzed by the National Research Council Canada (Ottawa, Ontario) for phytohormone content. The mixotrophic *Chlorella* whole cell samples were dried by drum, spray, refractance window, or freeze drying methods for analysis, and the results are reported with respect to dry weight (DW). A sample of mixotrophic *Chlorella* whole cells which was freeze dried before analysis was used as the closest approximation of the content of mixotrophic *Chlorella* cells that have not been subjected to a drying process.

The results of the sample analysis are shown in Tables 8-11, with n.d. indicating where the metabolite was not detected. The reported ng/g is equivalent to parts per billion (ppb) levels.

TABLE 8

| Mixotrophic *Chlorella* sp. Sample | ABA and ABA metabolites (ng/g DW) | | | | |
|---|---|---|---|---|---|
| | ABA | ABAGE | PA | DPA | t-ABA |
| Drum Dried | <3.8 | n.d. | n.d. | n.d. | n.d. |
| Spray Dried | <3.9 | <3.9 | n.d. | n.d. | n.d. |
| Refractance Window Dried | <4 | n.d. | n.d. | n.d. | n.d. |
| Freeze Dried | 31 | 33 | 16 | 60 | <3.9 |

The phytohormones in Table 8 are abbreviated as follows: ABA=cis-Abscisic acid; ABAGE=Abscisic acid glucose ester; PA=Phaseic acid; DPA=dihydrophaseic acid; and t-ABA=trans-Abscisic acid. As shown in Table 8, the drum dried, spray dried, and refractance window dried samples showed lower levels of ABA and ABA metabolites than the freeze dried sample.

TABLE 9

| Mixotrophic *Chlorella* sp. Sample | Cytokinins (ng/g DW) | | | | | | | |
|---|---|---|---|---|---|---|---|---|
| | t-ZOG | t-Z | c-Z | t-ZR | c-ZR | dhZR | iP | iPR |
| Drum Dried | n.d. | n.d. | n.d. | 3 | 119 | n.d. | <1 | 8 |
| Spray Dried | n.d. | n.d. | <1 | 3 | 111 | n.d. | <1 | 8 |
| Refractance Window Dried | n.d. | n.d. | <1 | 3 | 170 | n.d. | <1 | 9 |
| Freeze Dried | 10 | 5 | 94 | n.d. | <1 | n.d. | 41 | 5 |

The phytohormones in Table 9 are abbreviated as follows: t-ZOG=(trans) Zeatin-O-glucoside; t-Z=(trans) Zeatin; c-Z=(cis) Zeatin; t-ZR=(trans) Zeatin riboside; c-ZR=(cis) Zeatin riboside; dhZR=Dihydrozeatin riboside; iP=Isopentenyladenine; and iPR=Isopentenyladenosine. As shown in Table 9, the drum dried, spray dried, and refractance window dried samples showed higher levels of t-ZR, c-ZR, and iPR than the freeze dried sample. The freeze dried sample showed higher levels of t-ZOG, t-Z. c-Z, and iP than the other samples.

TABLE 10

| Mixotrophic *Chlorella* sp. Sample | Auxins (ng/g DW) | | | | |
|---|---|---|---|---|---|
| | IAA | IAA-Ala | IAA-Asp | IAA-Glu | IAA-Leu |
| Drum Dried | 154 | n.d. | n.d. | n.d. | <3.8 |
| Spray Dried | 234 | n.d. | n.d. | n.d. | n.d. |
| Refractance Window Dried | 122 | n.d. | n.d. | n.d. | <4 |
| Freeze Dried | 80 | n.d. | n.d. | n.d. | n.d. |

The phytohormones in Table 10 are abbreviated as follows IAA=Indole-3-acetic acid; IAA-Ala=N-(Indole-3-yl-acetyl)-alanine; IAA-Asp=N-(Indole-3-yl-acetyl)-aspartic acid; IAA-Glu=N-(Indole-3-yl-acetyl)-glutamic acid; and IAA-Leu=N-(Indole-3-yl-acetyl)-leucine. As shown in Table 10, the highest levels of IAA were in the spray dried sample, followed by the drum dried, refractance window dried, and freeze dried.

TABLE 11

| Mixotrophic Chlorella sp. Sample | Gibberellins (ng/g DW) | | | | | | | |
|---|---|---|---|---|---|---|---|---|
| | GA3 | GA4 | GA7 | GA8 | GA19 | GA34 | GA51 | GA53 |
| Drum Dried | <3.8 | n.d. | <3.8 | n.d. | n.d. | n.d. | n.d. | n.d. |
| Spray Dried | <3.9 | <3.9 | n.d. | <3.9 | n.d. | <3.9 | <3.9 | n.d. |
| Refractance Window Dried | n.d. | n.d. | n.d. | n.d. | n.d. | n.d. | n.d. | n.d. |
| Freeze Dried | n.d. | n.d. | <3.9 | <3.9 | 10 | <3.9 | n.d. | n.d. |

The phytohormones in Table 11 are abbreviated as follows: GA=Gibberellins. As shown in Table 11, the only significant detection of a Gibberellin was GA19 in the freeze dried sample.

Example 3

Samples of mixotrophic *Chlorella* whole cells were drum dried and analyzed by Food Safety Net Services (258 W. Turbo, San Antonio, Tex.) for nutritional content. The results of the analysis are show in Table 12.

TABLE 12

| Component | Concentration (per 100 g of biomass dry weight) |
|---|---|
| Ash | 2.4 g |
| Carbohydrates | 51.8 g |
| Calcium | 217.7 mg |
| Iron | 11.1 mg |
| Sodium | 50.5 mg |
| Protein | 30.9 g |
| Monounsaturated Fat | 3.3 g |
| Polyunsaturated Fat | 5.5 g |
| Saturated Fat | 3.1 g |

Example 4

An experiment was conducted to determine if application of a low concentration of a dried mixotrophic *Chlorella* based composition to tomato seeds planted in soil affected the rate at which the seedlings emerge from the soil. Tomatoes are part of the Solanaceae family. Tomato seeds (*Solanum lycopersicum*) were planted in trays with standard soilless plant potting soil mix. One treatment was compared to an untreated control (UTC) and is listed in Table 13. The treatment consisted of a mixotrophic *Chlorella* based composition which had been dried by a drum drier (DD) before formulation for treatment. Data showing the comparison of dried mixotrophic *Chlorella* to wet mixotrophic *Chlorella* treatments can be found in previously filed PCT application no. US2015/066160.

TABLE 13

| Treatment No. | Treatment Description |
|---|---|
| 1 | UTC - untreated water check |
| 2 | Mixotrophic *Chlorella* sp. - Drum Dried Whole Cells (DD) |

The treatment was pasteurized, normalized to 10% solids (for treatments with microalgal solids), and stabilized with phosphoric acid ($H_3PO_4$) and potassium sorbate ($C_6H_7KO_2$), with the remaining balance consisting of water. The mixotrophic *Chlorella* cells s were previously frozen and thawed, and were incorporated into the formulated treatment used in this experiment after cold storage following being harvested from the microalgae culturing system. The mixotrophic *Chlorella* based composition used in the treatment of this experiment was not analyzed to quantify bacteria in the composition, however aerobic plate counts for previous compositions of wet microalgae prepared with the same components in the same manner contained 40,000-36,000,000 CFU/mL.

The treatment was applied to the seeds at the low concentration of 4.73 mL/gallon. The treatment method consisted of drenching the soil at a rate of 100 gallons/acre using a watering can. The treatment was applied immediately after planting the seeds. The tested concentration of 4.73 mL/gallon diluted the composition which originally contained 10% solids by weight of mixotrophic *Chlorella* whole cells to the low percent solids content of only 0.012495%.

Each treatment was applied to 100 seeds planted in a 10 by 10 pattern in planting trays, with each row of ten counting as a replicate (10 total replicates). Visual observations were made daily to record the percentage of plants that have emerged from the soil. The standard used for assessing emergence was the hypocotyl stage where a stem was visible to be protruding from the potting soil mix. The experiment was conducted inside a greenhouse with all seeds and treatments subjected to the same controlled conditions including temperature and light. All trays were treated with the same amount of water throughout the experiment. No additional nutrients were provided to the plants during the experiment. All data rated as significant was done so utilizing the New Duncan's Multiple Test Range at a 90% confidence level, such that values with a statistical significant identifier of the same letter are not significantly different.

Results are shown in Table 14-16 with accompanying statistical significance grouping identifiers.

TABLE 14

| | Plant Emergence (Ave. % of plants emerged on date) | | | | | |
|---|---|---|---|---|---|---|
| | Day 1 | | Day 2 | | Day 3 | |
| | AM | PM | AM | PM | AM | PM |
| 1 | 0 a | 0 c | 0 D | 2 f | 3 d | 16 d |
| 2 | 0 a | 0 c | 0 D | 1 f | 2 d | 21 d |

TABLE 15

| | Plant Emergence (Ave. % of plants emerged on date) | | | | | |
|---|---|---|---|---|---|---|
| | Day 4 | | Day 5 | | Day 6 | Day 7 |
| | AM | PM | AM | PM | PM | PM |
| 1 | 17 g | 47 g | 55 e | 76 a | 83 a | 84 a |
| 2 | 24 g | 55 fg | 56 e | 77 a | 84 a | 87 a |

As shown in Tables 14-15, the treatment comprising drum dried *Chlorella* was comparable to the untreated control for plant emergence on a daily basis.

TABLE 16

| | Plant Emergence (Ave. % of plants emerged at observation time) | |
|---|---|---|
| | Untreated Control (UTC) | Mixotrophic *Chlorella* DD (Treatment 2) |
| Day 1 AM | 0 a | 0 a |
| Day 1 PM | 0 c | 0 c |
| Day 2 AM | 0 d | 0 d |
| Day 2 PM | 2 f | 1 f |
| % over UTC | | −50% |
| Day 3 AM | 3 d | 2 d |
| % over UTC | | −33% |
| Day 3 PM | 16 d | 21 d |
| % over UTC | | 31% |
| Day 4 AM | 17 g | 24 g |
| % over UTC | | 41% |
| Day 4 PM | 47 g | 55 fg |
| % over UTC | | 17% |
| Day 5 AM | 55 e | 56 e |
| % over UTC | | 2% |
| Day 5 PM | 76 a | 77 a |
| % over UTC | | 1% |
| Day 6 PM | 83 a | 84 a |
| % over UTC | | 1% |
| Day 7 PM | 84 a | 87 a |
| % over UTC | | 4% |

As shown in Table 16, while the drum dried *Chlorella* treatment did not produce a statistically significant difference from the untreated control, the drum dried *Chlorella* demonstrated numerical increases of at least 17% on days 3 PM, 4 AM, and 4 PM. The peak numerical increase over the untreated control occurred at day 4 AM and comprised a 41% increase.

Example 5

An experiment was conducted to determine if applications of dried algae as a seed coat on petunia seeds affected the germination and maturation of petunia plants. Petunias are part of the Solanaceae family. Seeds of multiple varieties of petunias were used in this experiment. The petunia varieties were rider salmon deep, duo lavender, double cascade, and dreams midnight. Two seed coat treatments were used in the experiment and compared to a control. The treatments were 5% freeze dried mixotrophic *Chlorella* sp. biomass and 1% freeze dried mixotrophic *Chlorella* sp. biomass.

Each treatment was applied in three replicates, with the average of the three replicates being used to compare the experimental data. The data was recorded for all plants at day 10 for the following metrics: height of the plant (cm), leaf area index (BVI), germination (%), and leaf size (cm). The results are shown below in Tables 17-20.

TABLE 17

| | Average Plant Height (cm) | | | |
|---|---|---|---|---|
| | *Petunia* Variety | | | |
| Treatment | Rider Salmon Deep | Duo Lavender | Double Cascade | Dreams Midnight |
| Control | 49.6 | 50.6 | 52.8 | 53.5 |
| 5% *Chlorella* | 50.0 | 50.7 | 52.6 | 54.4 |
| 1% *Chlorella* | 50.2 | 51.4 | 52.7 | 54.4 |

As shown in Table 17, plant height showed little variance between treatments for each petunia variety.

TABLE 18

| | Germination (%) | | | |
|---|---|---|---|---|
| | *Petunia* Variety | | | |
| Treatment | Rider Salmon Deep | Duo Lavender | Double Cascade | Dreams Midnight |
| Control | 73 | 86 | 88 | 85 |
| 5% *Chlorella* | 78 | 91 | 92 | 81 |
| 1% *Chlorella* | 75 | 88 | 91 | 86 |

As shown in Table 18, all treatments showed an increase in germination over the control except for the 5% *Chlorella* treatment for the Dreams Midnight variety.

TABLE 19

| | Leaf Size (cm) | | | |
|---|---|---|---|---|
| | *Petunia* Variety | | | |
| Treatment | Rider Salmon Deep | Duo Lavender | Double Cascade | Dreams Midnight |
| Control | 19.6 | 34.7 | 59.6 | 33.6 |
| 5% *Chlorella* | 22.7 | 40.0 | 57.6 | 34.6 |
| 1% *Chlorella* | 19.0 | 41.3 | 62.9 | 36.4 |

As shown in Table 19, the *Chlorella* treatments showed in increase in leaf size over the control except for the 1% treatment for the Rider Salmon Deep variety and the 5% treatment for the Double Cascade variety.

TABLE 20

Leaf Area Index (BVI)

| Treatment | Petunia Variety | | | |
|---|---|---|---|---|
| | Rider Salmon Deep | Duo Lavender | Double Cascade | Dreams Midnight |
| Control | 153.2 | 191.5 | 357.9 | 208.5 |
| 5% Chlorella | 198.3 | 238.9 | 377.8 | 214.0 |
| 1% Chlorella | 169.7 | 245.6 | 328.1 | 211.6 |

As shown in Table 20, the treatments showed large increases in the leaf area index over the control in the Rider Salmon Deep and Duo Lavender varieties, with a smaller increase for the Dreams Midnight variety. For the Double Cascade variety, the 5% Chlorella showed an increase over the control for leaf area index.

Example 6

An experiment was conducted to determine if applications of dried microalgae to compost for transplanted petunias affected the flowering and growth of petunia plants. Petunias are part of the Solanaceae family. Fourteen treatments were used in the experiment and compared to a control. The treatments were 1%, 3%, and 5% (by volume) inclusion of mixotrophic Chlorella biomass dried by refractance window (RWD), freeze (FD), spray (SD), and drum (DD) drying methods in the compost mix. A treatment of dried residual Haematococcus pluvialis biomass (RH) that had previously been subjected to an oil extraction process was also tested at an inclusion percentage of 1% and 3% (by volume). The Haematococcus pluvialis was cultured in phototrophic culture conditions, and drum dried before the extraction process. The treatments consisted of mixing the volume of dried microalgae with soil mix comprised of 80% peat moss, 20% West+MPC compost mix. The treatments were applied to 19 week old petunia plant plugs in two liter pots.

Each treatment was applied in three replicates, with the average of the three replicates being used to compare the experimental data. Treatments were laid out in a randomized block design in a heated greenhouse on benches. Quality scores were assigned on four assessment dates (based on visual observations of the plants) at 5, 7, 8, and 11 weeks after application of the treatments. The results are shown below in Tables 21-22.

TABLE 21

Average Quality Score

| Chlorella Treatments | Assessment Date | | | |
|---|---|---|---|---|
| | 5 weeks | 7 weeks | 9 weeks | 11 weeks |
| Control (untreated) | 7.22 | 7.33 | 7.00 | 6.78 |
| 5% RWD | 8.11 | 7.78 | 7.33 | 7.00 |
| 3% RWD | 8.22 | 7.67 | 7.44 | 6.78 |
| 1% RWD | 7.22 | 7.56 | 7.00 | 6.56 |
| 5% FD | 8.33 | 7.56 | 7.67 | 6.78 |
| 3% FD | 8.33 | 7.78 | 7.22 | 6.78 |
| 1% FD | 8.22 | 7.89 | 7.56 | 6.89 |
| 5% SD | 6.89 | 5.22 | 7.11 | 7.78 |
| 3% SD | 7.33 | 6.44 | 7.89 | 7.89 |
| 1% SD | 7.89 | 7.78 | 7.11 | 6.78 |
| 5% DD | 6.67 | 5.44 | 7.33 | 8.00 |
| 3% DD | 7.56 | 7.11 | 7.44 | 7.33 |
| 1% DD | 7.67 | 7.56 | 7.22 | 6.78 |

As shown in Table 21, RWD had better quality initially at 3% and 5% inclusion, but all showed gradual decline over the four assessment dates. All quality scores for the RWD treatments of 3% and 5% were greater than or equal to the control. All quality scores for the FD treatments were greater than or equal to the control, but declined over the trial period. The quality scores for the SD at 1% declined over time, but at 3% and 5% the scores initially decline and then increased to levels exceeding the control. The quality scores for the DD at 1% declined over time, at 3% went up and down over time, and at 5% initially declined but then increased to levels exceeding the control.

As shown in Table 21, at the final assessment SD at 3% and 5%, and DD at 5% showed the best results. After 14 weeks, SD at 3% and 5%, and DD at 5% were observed to show healthy green foliage and the plants were still flowering. This suggests that there is a beneficial effect with treatments of 3% SD, 5% SD, and 5% DD mixotrophic Chlorella.

TABLE 22

Average Quality Score

| Treatments | Assessment Date | | | |
|---|---|---|---|---|
| | 5 weeks | 7 weeks | 9 weeks | 11 weeks |
| Control (untreated) | 7.22 | 7.33 | 7.00 | 6.78 |
| 3% RH | 7.33 | 6.67 | 7.00 | 6.89 |
| 1% RH | 7.44 | 7.00 | 6.78 | 6.67 |

As shown in Table 22, RH at 1% had the same or worse quality scores than the control for three out of the four assessments, and RH at 3% ended with a quality score higher than the control. Comparing the results of Tables 21 and 22, the RH at 1% treatment also had lower final quality scores than three out of the four Chlorella treatments, and RH at 3% had lower final quality scores than the SD and DD Chlorella treatments. 14 weeks after treatment, the RH treated plants judged to be less healthy than the Chlorella SD at 3% and 5%, and DD at 5% treatments.

Example 7

An experiment was conducted to evaluate the effects of different applications of dried Chlorella on the germination of industrial hemp seeds. The experiment was conducted in greenhouses located at Lexington, Ky. The experimental design was completely randomized with four replications. Each treatment was applied to an appropriate volume of potting soil (Jiffy-Mix) used to fill one 25-cell tobacco float tray. The soil and treatment were thoroughly mixed, and the trays were filled with the mixture. Each cell in the tray was planted with one seed of the variety 'Futura 75' industrial hemp. The trays were then floated on a greenhouse bench allowing for saturation of the tray cells. The treatments used in the experiment consisted of 1%, 3%, and 5% v/v of dried mixotrophically cultured Chlorella, and were compared to an untreated control.

Germination was counted and recorded at 3 PM local time each day after seeding until germination for each tray reached its maximum. Seeds were considered germinated when both cotyledons were fully visible. Data was recorded and analyzed as days to maximum germination per tray, mean seedling vigor rated 1-9 [wherein 9=maximum both at 5 and 8 days after seeding (DAS)], mean whole seedling dry weight (per tray), and mean % of total germination (number of germinated seeds in a tray/25*100). The experiment was repeated to produce data for two full runs. Results are shown in Tables 23 (run 1) and 24 (run 2) displaying the % difference of the mean values to the untreated control.

TABLE 23

Percent difference of the mean values to the untreated control

| Treatment | Days to Germination | % Germination | Seedling Vigor (5 days) | Seedling Vigor (8 days) | Dry Weight |
|---|---|---|---|---|---|
| 1% v/v | −11.8 | 0.0 | 0.0 | +4.0 | +4.1 |
| 3% v/v | −5.9 | 0.0 | +3.6 | +12.0 | +4.4 |
| 5% v/v | +5.9 | −5.3 | +3.6 | 0.0 | −8.0 |

TABLE 24

Percent difference of the mean values to the untreated control

| Treatment | Days to Germination | % Germination | Seedling Vigor (5 days) | Seedling Vigor (8 days) | Dry Weight |
|---|---|---|---|---|---|
| 1% v/v | 0.0 | +17.3 | −3.7 | −7.7 | +10.3 |
| 3% v/v | 0.0 | +16.0 | −3.7 | +7.7 | +55.2 |
| 5% v/v | 0.0 | +12.3 | −14.8 | −11.5 | +48.3 |

No detrimental effects were observed for the plants receiving treatments when compared to the untreated control. As shown in Table 23, numerical increases were seen for seedling vigor after 5 days (3% and 5% treatments, seedling vigor after 8 days (1% and 3% treatments), and dry weight (1% and 3% treatments). As shown in Table 24, numerical increases were seen for the % germination (all treatments), seedling vigor after 8 days (3% and 5% treatments), and dry weight (all treatments).

Example 8

Fabaceae (Leguminosae)

Experiments are conducted to test effects of application of a dried microalgae based composition to crop plants of the family Fabaceae (Leguminosae). Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-e) of the composition.

Example 9

Poaceae

Experiments are conducted to test effects of application of a dried microalgae based composition to crop plants of the family Poaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-e) of the composition.

Example 10

Roasaceae

Experiments are conducted to test effects of application of a dried microalgae based composition to crop plants of the family Roasaceae. Application is done as in other examples herein, such that, in various treatments, (a) seeds are wetted or soaked in the composition; ((b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-e) of the composition.

Example 11

Vitaceae

Experiments are conducted to test effects of application of a dried microalgae based composition to crop plants of the family Vitaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-e) of the composition.

Example 12

Brassicaeae (Cruciferae)

Experiments are conducted to test effects of application of a dried microalgae based composition to crop plants of the family Brassicaeae (Cruciferae). Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-e) of the composition.

Example 13

Caricaceae

Experiments are conducted to test effects of application of a dried microalgae based composition to crop plants of the family Caricaceae. Application is done as in other examples herein, such that, in various treatments, (a) seeds are wetted or soaked in the composition; ((b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-e) of the composition.

Example 14

Malvaceae

Experiments are conducted to test effects of application of a dried microalgae based composition to crop plants of the family Malvaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-e) of the composition.

Example 15

Sapindaceae

Experiments are conducted to test effects of application of a dried microalgae based composition to crop plants of the family Sapindaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-e) of the composition.

Example 16

Anacardiaceae

Experiments are conducted to test effects of application of a dried microalgae based composition to crop plants of the family Anacardiaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-e) of the composition.

Aspects of the Invention

In one non-limiting embodiment of the invention, a method of plant enhancement may comprises administering to a plant, seedling, or seed a composition treatment comprising 0.1-20% by volume of dried microalgae cells to enhance at least one plant characteristics. In further embodiments, the concentration of dried microalgae cells may be 1-5% by volume. In further embodiments, the microalgae cells may be dried by at least one method selected form the group consisting of: freeze drying, spray drying, drum drying, crossflow air drying, solar drying, thin film convection oven drying, vacuum shelf drying, pulse combustion drying, flash drying, furnace drying, belt conveyor drying, and refractance window drying.

In some embodiments, the microalgae cells may be dried by a drum drying method. In some embodiments, the microalgae cells may be dried by a freeze drying method. In some embodiments, the microalgae cells may be dried by a spray drying method. In further embodiments, the dried microalgae cells may comprise 1-8% moisture on a wet basis.

In further embodiments, the microalgae cells may be cultured in mixotrophic conditions. In some embodiments, the mixotrophic microalgae cells may comprise *Chlorella*. In some embodiments, the mixotrophic conditions may comprise culturing *Chlorella* cells in a suitable culture medium for a culture length of 7-14 days, at a temperature between 20 and 30° C., at a pH between 6.5 and 8.5, and a dissolved oxygen concentration between 0.1 and 4 mg/L. In some embodiments, the *Chlorella* cells may be cultured in non-axenic mixotrophic conditions. In some embodiments, the *Chlorella* cells may be cultured with acetic acid or acetate as the organic carbon source.

In further embodiments, the administering may be selected from: coating a seed with the composition prior to planting; soaking a seed in a solution of water and the composition prior to planting; contacting a solid growth medium in an immediate vicinity of a planted seed with an effective amount of the composition; contacting roots of a plant with an effective amount of the composition with an effective amount of the composition hydroponically; administering an effective amount to a solid growth medium prior to or after the planting of a seed, seedling, or plant; and mixing an effective amount of the composition in a suitable solid growth medium prior to planting a seed, seedling, or plant. In some embodiments, the solid growth medium may comprise at least one from the group consisting of: soil, potting mix, compost, or inert hydroponic material. In some embodiments, the composition may be administered to the solid growth medium by mixing the composition with water and distributing through a system selected from a low volume irrigation system, a soil drench application, and an aerial spraying system.

In further embodiments, the plant may be a member of a plant family selected from Solanaceae, Fabaceae (Leguminosae), Poaceae, Roasaceae, Vitaceae, Brassicaeae (Cruciferae), Caricaceae, Malvaceae, Sapindaceae, Anacardiaceae, Rutaceae, Moraceae, Convolvulaceae, Lamiaceae, Verbenaceae, Pedaliaceae, Asteraceae (Compositae), Apiaceae (Umbelliferae), Araliaceae, Oleaceae, Ericaceae, Actinidaceae, Cactaceae, Chenopodiaceae, Polygonaceae, Theaceae, Lecythidaceae, Rubiaceae, Paveraceae, Illiciaceae, Grossulariaceae, Myrtaceae, Juglandaceae, Bertulaceae, Cucurbitaceae, Asparagaceae (Liliaceae), Alliaceae (Liliceae), Bromeliaceae, Zingieraceae, Muscaceae, Areaceae, Dioscoreaceae, Myristicaceae, Annonaceae, Euphorbiaceae, Lauraceae, Peperaceae, and Proteaceae.

In further embodiments, the composition may further comprise water and at least one culture stabilizer suitable for plants. In some embodiments, the culture stabilizer may be selected from: potassium sorbate, phosphoric acid, ascorbic acid, sodium benzoate, citric acid, and any combination thereof. In some embodiments, the composition treatment may not contain an active ingredient for enhancing the plant characteristic other than the dried microalgae cells.

In further embodiments, the composition may further comprise at least one selected from the group consisting of: nitrogen, phosphorus, potassium, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium thulium, ytterbium, yttrium.

In some embodiments, enhancement of the at least one plant characteristic may be determined by comparison of a treated plant with a substantially identical untreated plant, and wherein a quantifiable different of at least 10% is observed for the at least one plant characteristic. In further embodiment the plant characteristic may be selected from: seed germination rate, seed germination time, seedling emergence, seedling emergence time, seedling size, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. In some embodiments, the plant characteristic may be selected from seed germination rate, seed germination time, seedling emergence, and seedling emergence time. In some embodiments, the plant characteristic may be selected from leaf formation, leaf size, and leaf area index. In some embodiments, the plant characteristic may be selected from plant quality, plant health, and flowering.

In another non-limiting embodiment, a composition may comprise dried mixotrophically cultured *Chlorella* cells suitable for application to plants, wherein the mixotrophically cultured *Chlorella* cells comprise 1-8% moisture on a wet basis. In further embodiments, the concentration of dried mixotrophically cultured *Chlorella* cells may be 0.1-20% by volume. In further embodiments, the composition may further comprise at least one of: nitrogen, phosphorus, potassium, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium.

In further embodiments, the composition may further comprise water. In further embodiments, the composition may further comprise soil, potting mix, compost, inert hydroponic material, or combinations thereof. In further embodiments, the composition may comprise at least one of a binder, filler, solvent, thickener, colouring agent, antifoaming agent, biocide, surfactant, and pigment suitable for a seed coating.

In some embodiments, the cells of the composition may be intact. In some embodiments, the cells of the composition may be lysed or disrupted. In further embodiments, the *Chlorella* cells may be cultured in non-axenic mixotrophic conditions. In some embodiments, the *Chlorella* cells may be cultured with acetic acid or acetate as an organic carbon source.

In another non-limiting embodiment, a method of preparing a composition may comprise; drying mixotrophically cultured microalgae cells to a moisture content of 1-8% on a wet basis; and storing the dried cells in a container. In further embodiments, the method may further comprise mixing the dried microalgae cells with at least one of a solid growth medium and water. In some embodiments, the at least one solid growth medium may be selected from the group consisting of: soil, potting mix, compost, and inert hydroponic material.

In some embodiments, the concentration of dried microalgae cells may be 0.1-20% by volume. In some embodiments, the container is a bag, bucket, jug, tote, or bottle. In further embodiments, the method may further comprise mixing the composition with at least one culture stabilizer suitable for plants. In some embodiments, the at least one culture stabilizer may be selected from: potassium sorbate, phosphoric acid, ascorbic acid, sodium benzoate, citric acid, and any combination thereof.

In further embodiments, the microalgae cells may comprise *Chlorella* cultured in mixotrophic conditions. In some embodiments, the *Chlorella* cells may be cultured with acetic acid or acetate as an organic carbon source. In some embodiments, the *Chlorella* cells may be cultured in non-axenic mixotrophic conditions.

In some embodiments, the microalgae cells may be dried by at least one method selected from the group consisting of: freeze drying, spray drying, drum drying, crossflow air drying, solar drying, thin film convection oven drying, vacuum shelf drying, pulse combustion drying, flash drying, furnace drying, belt conveyor drying, and refractance window drying. In some embodiments, the microalgae cells may be dried by a drum drying method. In some embodiments, the microalgae cells may be dried by a freeze drying method. In some embodiments, the microalgae cells may be dried by a spray drying method.

In further embodiments, the method may further comprise mixing the dried microalgae cells with at least one other component suitable for coating seeds. In further embodiments, the method may further comprise mixing the dried microalgae cells with at least one selected from the group consisting of: nitrogen, phosphorus, potassium, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium.

In another non-limiting embodiment, a method of making a composition for enhancing a characteristic of a plant may comprise: subjecting microalgae cells to a drying means to produce dried microalgae cells with a moisture content of 1-15%; and forming a composition comprising 0.1-20% by volume of dried microalgae cells, wherein the composition is suitable to administer to a plant, seedling, or seed to enhance at least one plant characteristic. In further embodiments, the drying means may lyse or disrupt the microalgae cells. In further embodiments, the drying means may increase the pore size of the microalgae cells. In further embodiments, the drying means may reduce at least one of protein and pigment concentrations of the microalgae cells.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

What is claimed is:

1. A method of plant enhancement comprising administering to a plant, seedling, or seed a composition comprising 0.1-1% solids by weight of dried *Chlorella* cells to enhance at least one plant characteristic,
   wherein the dried *Chlorella* cells are pasteurized and the at least one plant characteristic is seedling size, plant fresh weight, plant dry weight, leaf production, leaf formation, leaf size, leaf area index, root length, or root mass.

2. The method of claim 1, wherein the *Chlorella* cells are dried by at least one method selected from the group consisting of: freeze drying, spray drying, drum drying, crossflow air drying, solar drying, thin film convection oven drying, vacuum shelf drying, pulse combustion drying, flash drying, furnace drying, belt conveyor drying, and refractance window drying.

3. The method of claim 1, wherein the *Chlorella* cells are cultured in mixotrophic conditions, wherein the mixotrophic conditions comprise culturing *Chlorella* cells in a suitable culture medium for a culture length of 7-14 days, at a temperature between 20 and 30° C., at a pH between 6.5 and 8.5, and a dissolved oxygen concentration between 0.1 and 4 mg/L.

4. The method of claim 3, wherein the *Chlorella* cells are cultured in non-axenic mixotrophic conditions and are cultured with acetic acid or acetate as the organic carbon source.

5. The method of claim 1, wherein the administering step is selected from the group consisting of: coating a seed with the composition prior to planting; soaking a seed in a solution of water and the composition prior to planting; contacting a solid growth medium in an immediate vicinity of a planted seed with an effective amount of the composition; contacting roots of a plant with an effective amount of the composition hydroponically; administering an effective amount to a solid growth medium prior to or after the planting of a seed, seedling, or plant; and mixing an effective amount of the composition in a suitable solid growth medium prior to planting a seed, seedling, or plant, wherein the solid growth medium comprises at least one from the group consisting of: soil, potting mix, compost, or inert hydroponic material.

6. The method of claim 5, wherein the composition is administered to the solid growth medium by mixing the composition with water and distributing through a system selected from a low volume irrigation system, a soil drench application, and an aerial spraying system.

7. The method of claim 1, wherein the plant is a member of a plant family selected from: Solanaceae, Fabaceae (Leguminosae), Poaceae, Roasaceae, Vitaceae, Brassicaeae (Cruciferae), Caricaceae, Malvaceae, Sapindaceae, Anacardiaceae, Rutaceae, Moraceae, Convolvulaceae, Lamiaceae, Verbenaceae, Pedaliaceae, Asteraceae (Compositae), Apiaceae (Umbelliferae), Araliaceae, Oleaceae, Ericaceae, Actinidaceae, Cactaceae, Chenopodiaceae, Polygonaceae, Theaceae, Lecythidaceae, Rubiaceae, Paveraceae, Illiciaceae, Grossulariaceae, Myrtaceae, Juglandaceae, Bertulaceae, Cucurbitaceae, Asparagaceae (Liliaceae), Alliaceae (Liliceae), Bromeliaceae, Zingieraceae, Muscaceae, Areaceae, Dioscoreaceae, Myristicaceae, Annonaceae, Euphorbiaceae, Lauraceae, Peperaceae, and Proteaceae.

8. The method of claim 1, wherein the composition further comprises water and at least one stabilizer suitable for plants selected from the group consisting of: potassium sorbate, phosphoric acid, ascorbic acid, sodium benzoate, and citric acid.

9. The method of claim 1, wherein the composition further comprises at least one selected from the group consisting of: nitrogen, phosphorus, potassium, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium.

10. The method of claim 1, wherein the plant characteristic is seedling size.

11. The method of claim 1, wherein the dried *Chlorella* cells comprise 1-8% moisture on a wet basis.

12. A method of enhancing at least one plant characteristic comprising administering an effective amount of a composition comprising 1-5% solids by weight of dried *Chlorella* cells to a plant, seedling, or seed,
   wherein the presence of the dried *Chlorella* cells in the composition enhances the at least one plant characteristic of the plant compared to a composition lacking the dried *Chlorella* cells, the dried *Chlorella* cells are pasteurized, and the at least one plant characteristic is seedling size, plant fresh weight, plant dry weight, leaf production, leaf formation, leaf size, leaf area index, root length, or root mass.

13. The method of claim 12, wherein the composition comprises 3-5% solids by weight of dried *Chlorella* cells.

14. The method of claim 12, wherein the administering step comprises:
mixing the dried *Chlorella* cells with water to make a liquid composition; and
contacting soil in the immediate vicinity of a planted seed, seedling, or plant with the liquid composition.

15. The method of claim 14, wherein the liquid composition was pasteurized at a temperature in the range of 50-90° C. for a period of time in the range of 90-150 minutes.

16. The method of claim 12, wherein the administering step comprises:
mixing the dried *Chlorella* cells with at least one of a binder, filler, solvent, thickener, colouring agent, antifoaming agent biocide, surfactant, and pigment to make a seed coating; and
coating a seed with the seed coating prior to planting the seed.

17. The method of claim 12, wherein the administering step comprises:
mixing the dried *Chlorella* cells with a solid growth medium to make a mixture, wherein the solid growth medium comprises at least one from the group consisting of: soil, potting mix, compost, or inert hydroponic material; and
planting a seed, seedling, or plant within the mixture.

18. The method of claim 12, wherein the *Chlorella* cells are dried by at least one method selected from the group consisting of: freeze drying, spray drying, drum drying, crossflow air drying, solar drying, thin film convection oven drying, vacuum shelf drying, pulse combustion drying, flash drying, furnace drying, belt conveyor drying, and refractance window drying.

19. The method of claim 12, wherein the plant is a member of a plant family selected from: Solanaceae, Fabaceae (Leguminosae), Poaceae, Roasaceae, Vitaceae, Brassicaeae (Cruciferae), Caricaceae, Malvaceae, Sapindaceae, Anacardiaceae, Rutaceae, Moraceae, Convolvulaceae, Lamiaceae, Verbenaceae, Pedaliaceae, Asteraceae (Compositae), Apiaceae (Umbelliferae), Araliaceae, Oleaceae, Ericaceae, Actinidaceae, Cactaceae, Chenopodiaceae, Polygonaceae, Theaceae, Lecythidaceae, Rubiaceae, Paveraceae, Illiciaceae, Grossulariaceae, Myrtaceae, Juglandaceae, Bertulaceae, Cucurbitaceae, Asparagaceae (Liliaceae), Alliaceae (Liliceae), Bromeliaceae, Zingieraceae, Muscaceae, Areaceae, Dioscoreaceae, Myristicaceae, Annonaceae, Euphorbiaceae, Lauraceae, Peperaceae, and Proteaceae.

20. The method of claim 12, wherein the composition further comprises at least one selected from the group consisting of: nitrogen, phosphorus, potassium, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium.

* * * * *